(12) United States Patent
Frangioni et al.

(10) Patent No.: US 7,394,053 B2
(45) Date of Patent: Jul. 1, 2008

(54) SYSTEMS AND METHODS FOR MULTI-MODAL IMAGING HAVING A SPATIAL RELATIONSHIP IN THREE DIMENSIONS BETWEEN FIRST AND SECOND IMAGE DATA

(75) Inventors: John V. Frangioni, Wayland, MA (US); Roberto Accorsi, Radnor, PA (US); Richard C. Lanza, Brookline, MA (US); John Idoine, Mt. Vernon, OH (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 11/222,864

(22) Filed: Sep. 9, 2005

(65) Prior Publication Data

US 2006/0108509 A1 May 25, 2006

Related U.S. Application Data

(60) Provisional application No. 60/609,197, filed on Sep. 9, 2004.

(51) Int. Cl.
*H01L 27/00* (2006.01)
(52) U.S. Cl. .................................. 250/208.1; 250/226
(58) Field of Classification Search ................. 600/407, 600/424–426, 410, 414; 250/363.04, 208.1, 250/226, 201.3, 363.02–363.06; 382/128, 382/131; 128/922
See application file for complete search history.

(56) References Cited

U.S. PATENT DOCUMENTS 5,245,191 A * 9/1993 Barber et al. .......... 250/363.04
6,737,652 B2   5/2004 Lanza et al.
6,806,475 B1 * 10/2004 Lightfoot et al. ............. 250/395
6,920,346 B2 * 7/2005 Kazandjian et al. ......... 600/420
7,094,203 B2 * 8/2006 Inoue et al. .................. 600/439
2003/0036699 A1 * 2/2003 Strauss ....................... 600/436

(Continued)

FOREIGN PATENT DOCUMENTS

WO     WO 3025621 A1 *  3/2003

OTHER PUBLICATIONS

Accorsi et al., "A coded Aperture for High-Resolution Nuclear Medicint Planar Imaging With a Conventional Anger Camera: Experimental Results", IEEE Transactions on Nuclear Science, vol. 48, No. 6, pp. 2411-2417, Dec. 2001.

(Continued)

*Primary Examiner*—Que T Le
(74) *Attorney, Agent, or Firm*—Fish & Richardson P.C.

(57) ABSTRACT

The invention relates to imaging systems that include a coded aperture detection system and an optical detection system. The coded aperture detection system is configured to detect radiation emitted by a radionuclide present within an object and to provide a first detector signal from the detected radiation. The optical detection system is configured to detect optical radiation from the object and to provide a second detector signal from the detected optical radiation. The system also includes a processor configured to prepare first image data from the first detector signal, second image data from the second detector signal, and registered data indicative of a spatial relationship in at least one dimension between the first and second image data. The invention also includes methods of using the new systems, e.g., for sentinel lymph node mapping and tissue resection.

22 Claims, 6 Drawing Sheets

U.S. PATENT DOCUMENTS

2004/0152975 A1* 8/2004 Blevis .................. 600/427
2007/0040124 A1 2/2007 Accorsi

OTHER PUBLICATIONS

Accorsi et al., "Near Field Artifact Reduction in Planar Coded Aperture Imaging", Applied Optics, vol. 40, No. 26, pp. 4697-4705, Sep. 10, 2001.

English et al., "Sub-Millimeter Technetium-99m Calibration Sources", Molecular Imaging and Biology, vol. 4, No. 5, pp. 380-384, 2002.

Funovics et al., "Catheter-Based in Vivo Imaging of Enzyme Activity and Gene Expression: Feasibility Study in Mice", Molecular Imaging, Radiology, pp. 659-666, Jun. 2004.

Grand et al., "An Operational Near-Infrared Fluorescent Imaging System Prototype for Large Animal Survey", Technology in Cancer Research & Treatment, vol. 2, No. 6, Dec. 2003.

Kim et al., "Near-Infrared Fluorescent Type II Quantum Dots for Sentinel Lymph Node Mapping", Nature Biotechnology, Dec. 7, 2003.

Lim et al., "Selection of Quantum Dot Wavelengths for Biomedical Assays and imaging", Molecular Imaging, vol. 2, No. 1, pp. 50-64, Jan. 2003.

Schellingerbout et al., "Coded Aperture Nuclear Scintigraphy: A Novel Small Animal Imaging Technique", Molecular Imaging, vol. 1, No. 4, pp. 344-353, Oct. 2002.

Ziock et al., "Source-Search Sensitivity of a Large-Area, Coded-Aperture, Gamma-Ray Imager", IEEE Nuclear Science Symposium and Medical Imaging Conference, Rome, Italy, Oct. 17-23, 2004.

* cited by examiner

SYSTEMS AND METHODS FOR MULTI-MODAL IMAGING HAVING A SPATIAL RELATIONSHIP IN THREE DIMENSIONS BETWEEN FIRST AND SECOND IMAGE DATA

CROSS-REFERENCE TO RELATED APPLICATION

This application claims priority from U.S. Provisional Patent Application Ser. No. 60/609,197, filed on Sep. 9, 2004, which is incorporated herein by reference in its entirety.

FEDERALLY SPONSORED RESEARCH

This invention was made with government support under Grant Number DAAD07-98-C-0117, awarded by the Army, and Grant Number 93-G-053, awarded by the Department of Transportation. The government thus has certain rights in the invention.

FIELD OF THE INVENTION

The present invention relates to methods and systems for obtaining images of one or more portions of objects, e.g., one or more portions of a human or animal.

BACKGROUND

Medical imaging can provide health professionals with information about the anatomy, physiology, and histology of humans and animals. Images can be displayed and acquired in both two and three dimensions. In some imaging procedures, a contrast agent is used to accentuate differences between a region of interest and surrounding tissues. Some contrast agents, for example, have an affinity for particular types of tissues or cells, e.g., cancerous cells. When introduced to a subject, the contrast agent tends to concentrate near cancerous cells allowing the visualization of otherwise hidden cancers. Other contrast agents may lack a particular affinity for a particular cell or tissue. Such contrast agents may be used to, e.g., visualize pathways such as vessels and lymph ducts.

One application of medical imaging is to perform sentinel lymph node (SNL) mapping. In this technique, a health professional seeks to identify lymph nodes associated with a cancerous tumor. The underlying hypothesis behind SNL mapping is that the first lymph node, defined as the SLN, to receive lymphatic drainage from a tumor site will exhibit tumors if there has been lymphatic spread. If no malignant cells are found in the SLN during frozen section analysis in the operating room, then the patient is spared the significant morbidity associated with a radical dissection of all lymph nodes surrounding the tumor. In breast cancer, for example, auxiliary node dissection, and its associated lymphedema, can be avoided in patients whom the SLN is negative histologically. Another benefit of SLN mapping is that it affords a regional control in patients with palpable tumor-containing nodes.

Sentinel lymph node mapping and resection are presently the standard of care for both breast cancer and melanoma. Although tumors that are already malignant at the time of resection may not benefit from SLN mapping, large clinical studies have shown that only approximately 5% of SLN-negative breast cancer patients will manifest metastatic disease at a later time. These results suggest that SLN mapping and resection may be a reasonable approach for most solid tumors, and indeed, clinical studies in colon cancer have already begun.

SUMMARY

One aspect of the present invention relates to systems that can obtain and optionally display multi-modal images, e.g., at least one optical image and at least one radioscintigraphic image, of an object, e.g., a tissue and/or organ of a subject, such as a human or animal. In general, the system can display the images in a manner that allows a user to visualize a spatial relationship between the images. For example, the images can be displayed as superimposed images. The object may be a near field object.

In some embodiments, the optical image is a visible light and/or fluorescence image, e.g., a fluorescence image indicative of a distribution of a fluorescent compound within the object. Typically, the fluorescent compound is an exogenous fluorescent contrast agent introduced into the object. The fluorescent image can be indicative of fluorescence in the near-infrared and/or infrared wavelength ranges.

In certain embodiments, the radioscintigraphic image is indicative of a distribution of a radionuclide within the object. Typically, the radionuclide is a gamma ray-emitting contrast agent introduced into the object. The fluorescent contrast agent and radioscintigraphic contrast agent may be, but are not necessarily, the same compound.

In some embodiments, a reflected light image is obtained as an alternative or addition to the fluorescent image of the object. In either case, the reflected light image, the radioscintigraphic image, and, optionally, the fluorescence image, can be displayed in a manner that allows a user to visualize a spatial relationship between the images. For example the images can be displayed as superimposed images.

Another aspect of the present invention relates to methods for obtaining an optical image and a radioscintigraphic image of an object, e.g., a tissue and/or organ of a human or animal subject. A fluorescent compound is introduced directly or indirectly into the object. A radionuclide is introduced into the object. For example, the fluorescent contrast agent and radionuclide can be introduced by injection. Thereafter, an optical image indicative of a distribution of the fluorescent compound, and a radioscintigraphic image indicative of a distribution of the radionuclide are obtained, and the images are displayed in a manner that allows a user to visualize a spatial relationship between the images. For example, the images can be displayed as superimposed images.

In certain embodiments, the new imaging systems include a near-field coded aperture detection system configured to detect radiation emitted by a radionuclide present within an object and to provide a first detector signal from the detected radiation and an optical detection system configured to detect optical radiation from the object and to provide a second detector signal from the detected optical radiation. The system also includes a processor configured to prepare first image data from the first detector signal, prepare second image data from the second detector signal, and prepare registered data indicative of a spatial relationship in at least one dimension between the first and second image data. For example, the registered data can be prepared from the first and second image data.

The system can include a display and be configured to display an image including, superimposed with one another, the first and second image data registered in at least one dimension. The image may be a two-dimensional image and the one dimension may be generally perpendicular to the image. A resolution of first image data along the one dimension can be less than about 10 cm, e.g., less than about 2.5 cm or 100 cm, with respect to the object. The first image data may be indicative of a distribution of the radionuclide within a two-dimensional slice through the object.

Radiation emitted by the radionuclide and detected by the near-field coded aperture detection system can propagate generally along a detection axis and the one dimension may be generally aligned with the detection axis. A resolution of first image data along the one dimension may be less than about 10 cm, e.g., less than about 2.5 cm or 1.0 cm, with respect to the object. The near-field coded aperture detection system can detect radiation from a radionuclide present at each of a plurality of distances along the detection axis and the first image data may be indicative of the distribution of a radionuclide within the object at a selected distance along the detection axis. The processor can be configured with an iterative algorithm for preparing the first image data.

In some embodiments, the second detector signal can be indicative of a reflected light image of the object.

The optical detection system can be configured to irradiate the object with light and to detect fluorescence emitted from the object and the second image data can be indicative of the fluorescence emitted from the object. The optical detection system can be configured to detect fluorescence having a wavelength in the near-infrared, and/or infrared, wavelength ranges. The displayed, superimposed first and second image data can be indicative of the spatial relationship between the distribution of the radionuclide within the object and the distribution of fluorescence from the object.

The coded aperture detection system can be configured to detect radiation emitted by an isotope of fluorine, indium, and/or an isotope of technetium. A field of view of the coded aperture detection system and a field of view of the optical detection system can simultaneously include an identical portion of the object. In various embodiments, the imaging system can be configured to detect gamma radiation having an energy of between about 500 keV and about 520 keV, e.g., 511 keV radiation.

The imaging systems can be configured to provide a third detector signal by detecting third radiation from the object, the third radiation having an energy different from an energy of the radiation emitted by the radionuclide and from an energy of the optical radiation. The third radiation may include visible light and the processor can be configured to prepare third image data from the third detector data and display the third image data simultaneously with the first and second image data.

In another embodiment, the invention features imaging systems configured to obtain image data indicative of a spatial relationship, within a portion of a human or animal, between (a) a distribution of at least one radionuclide and (b) a distribution of at least one fluorescent compound, the fluorescent compound having a fluorescence maximum in at least one of the near-infrared (near-IR) or infrared (IR) wavelength ranges. The imaging system can include a near-field coded aperture detection system including a coded aperture plate including a plurality of apertures and being configured to receive radiation emitted by at least one radionuclide within the portion of the human or animal. The system can also include a detector configured to (a) detect, in at least two dimensions, radiation emitted by at least one radionuclide and transmitted by the apertures of the coded aperture plate and (b) provide a first detector signal indicative of the detected radiation, an optical detection system, including an excitation source configured to excite fluorescence from at least one fluorescent compound within the portion of the human or animal, an imaging detector configured to (a) detect optical radiation emitted by at least one fluorescent compound and (b) provide a second detector signal indicative of the detected optical radiation, and a processor configured to receive the first and second detector signals and to prepare image data indicative of a spatial relationship, within the portion of the human or animal, between (a) the distribution of at least one radionuclide and (b) the distribution of at least one fluorescent compound.

Another aspect of the invention relates to imaging methods. These methods include introducing a radionuclide into a portion of a human or animal, providing, e.g., by detecting, a first detector signal indicative of radiation that was emitted by the radionuclide from the portion of the human or animal and transmitted by apertures of a coded aperture array, providing, e.g., by detecting an optical signal, optical image data indicative of an optical image of the portion of a human or animal, and preparing multi-image data indicative of a spatial relationship in at least one dimension between a distribution of the radionuclide within the portion of the human or animal and the optical image thereof. In a last step, the multi-image data can be displayed.

The radionuclide can emit a gamma-ray having an energy of from about 70 keV to about 525 keV, e.g., about 511 keV.

In another embodiment, the invention features imaging methods for preparing image data indicative of a spatial relationship within a portion of a human or animal, between a distribution of at least one radionuclide and a distribution of at least one fluorescent compound, the fluorescent compound having a fluorescence maximum in at least one of the near-infrared (near-IR) or infrared (IR) wavelength ranges. The methods include introducing at least one radionuclide into a portion of a human or animal, introducing at least one fluorescent compound into the portion of the human or animal, providing a first detector signal indicative of radiation that was emitted by the radionuclide from the portion of the human or animal and transmitted by apertures of a coded aperture array, providing fluorescence image data indicative of a distribution of the fluorescent compound within the portion of the human or animal, and preparing and/or displaying multi-image data indicative of a spatial relationship, within the portion of the human or animal, between a distribution of the radionuclide and the distribution of the fluorescent compound.

The portion of the subject, e.g., human or animal, can be, for example, breast tissue, heart tissue, brain tissue, or other organ tissue, or tissue in the vicinity of lymph nodes, which may be sentinel lymph nodes (SLNs). The human subject can be a patient diagnosed with cancer, e.g., in need of SLN mapping or tissue resection. The animal can be, for example, a domesticated animal, such as a horse, cow, pig, sheep, goat, dog, or cat, a laboratory animal, such as a mouse, rat, pig, or a wild animal, such as a monkey or ape. Animals also include, for example, birds, reptiles, and amphibians.

Another aspect of the invention relates to calibration standards for calibrating an imaging system including a plurality of spaced-apart calibration sites, each calibration site including a first compound detectable by a first imaging modality and a second compound detectable by a second imaging modality. The first and second imaging modalities can include fluorescence and radioscintigraphy, and the calibration sites can include a fluorescent compound and a radionuclide. In some embodiments, each site exhibits a fluorescence equivalent to 10 nM indocyanine green in dimethyl sulfoxide at an excitation wavelength of 780 mn and detection at 820 nm. Each site can have a gamma ray activity of at least 1 µCi.

The calibration standards can have the fluorescent compound and radionuclide mutually distributed within a given calibration site. The calibration standards include a first set of calibration sites defining a first plane and a second set of calibration sites defining a second, different plane. For example, the first and second planes can be substantially parallel and can be spaced apart by between about 2 mm and about 3 cm. In certain embodiments, the calibration standards can have calibration sites supported by a substrate that is substantially transparent at a wavelength corresponding to the fluorescence maximum of the fluorescent compound. The calibration sites can include a polymer and the fluorescence compound and gamma ray-emitting compound are associated with the polymer. For example, the polymer can be an ion exchange resin.

The fluorescent compound and radionuclide can be mutually distributed within a given calibration site, i.e., the spatial distribution of the fluorescent compound and radionuclide can be the same. In some embodiments, the standards can include a first set of calibration sites defining a first plane and a second set of calibration sites defining a second, different plane. The first and second sets can include, e.g., 3 sites, 4 sites, 5 sites, or even more sites. The number of sites can be different in each set.

Another aspect of the invention relates to resection methods including (a) introducing a radionuclide to a subject, such as a human patient, (b) obtaining a first radioscintigraphic image indicative of a distribution of the radionuclide within a portion of the patient, (c) removing an amount of tissue from the patient based on the first radioscintigraphic image, (d) obtaining an additional radioscintigraphic image indicative of a distribution of radionuclide remaining within the portion of the patient, and (e) removing an amount of tissue from the patient based on the additional radioscintigraphic image. These methods can include obtaining optical, e.g., visible and/or fluorescent, images from the subject, and superimposing or otherwise registering the optical and radioscintigraphic images, and optionally displaying the superimposed image.

Another aspect of the invention relates to radioscintigraphic methods including introducing a radionuclide to a human and imaging, using a coded aperture mask, a tissue, such as the breast tissue of the human to obtain an image indicative of a distribution of the radionuclide within the breast. The radionuclide can include a positron emission tomography pharmaceutical. The radionuclide can include $^{18}$F. These methods can also include obtaining optical, e.g., visible (e.g., color video) and/or fluorescent, images of the same tissue and viewing the images as multi-modal images.

In yet another aspect, the invention includes methods for processing radioscintigraphic data by providing coded aperture data indicative of a distribution of a radionuclide within an object, the coded aperture data having been obtained by detecting radiation emitted by the radionuclide and transmitted by a mask having a plurality of transparent portions arranged within a substrate, a first portion of the detected radiation having been transmitted by the transparent portions of the mask, a second portion of the detected radiation having been transmitted by the substrate of the mask; and creating an image of the distribution of the radionuclide based on the first portion of the detected radiation. These methods can include correcting the coded aperture data for the presence of the second portion of the detected radiation. For example, the correcting can include subtracting the second portion of the detected radiation from the coded aperture data.

The second portion of the detected radiation can be determined, for example, by detecting radiation from an amount of the radionuclide (a) with the mask intermediate the amount of radionuclide and the detector and (b) with the mask not intermediate the amount of radionuclide and the detector and comparing radiation detected in (a) and (b). In addition, the coded aperture data can be obtained by detecting radiation emitted by the radionuclide and transmitted by the mask.

The invention also includes other methods for processing radioscintigraphic data by providing coded aperture data indicative of a distribution of a radionuclide within an object, the coded aperture data having been obtained by detecting radiation emitted by the radionuclide and transmitted by a mask having a plurality of transparent portions arranged within a substrate, a first portion of the detected radiation having been transmitted by the transparent portions of the mask, a second portion of the detected radiation having been transmitted by the substrate of the mask; and subtracting a value from the coded aperture data, the value being indicative of the amount of radiation transmitted by the substrate of the mask.

The new imaging systems include an optical imaging system and a coded aperture radioscintigraphic imaging system allowing optical image data sets, including one or both of reflected light and fluorescence images, and radioscintigraphic image data sets to be acquired simultaneously, scaled, co-registered and displayed in essentially real-time for an operator, e.g., a surgeon. The imaging systems combine the high sensitivity and volumetric capabilities of radioscintigraphic imaging, which can sometimes fail to represent anatomical landmarks, with the high resolution and specificity afforded by fluorescence imaging. In addition, the new systems and methods combine two-dimensional and three-dimensional images to provide surgeons and other users ultra-sensitive, highly specific image guidance. For example, the new systems and methods advantageously provide real-time visual guidance for the localization of a tissue, such as sentinel lymph nodes, and of lymph flow in three dimensions and post-resection inspection of the surgical field. By combining anatomically informative images with images indicative of fine structures such as blood vessels and nerves, the likelihood for injury to subjects undergoing procedures can be significantly reduced.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 4c is a second perspective side view of the tissue and beads of FIG. 4a.

FIG. 7A shows the image obtained with a clinical pET/CT scanner, and FIG. 7B shows an image obtained using the new systems and methods described herein.

DETAILED DESCRIPTION

Figure 1:
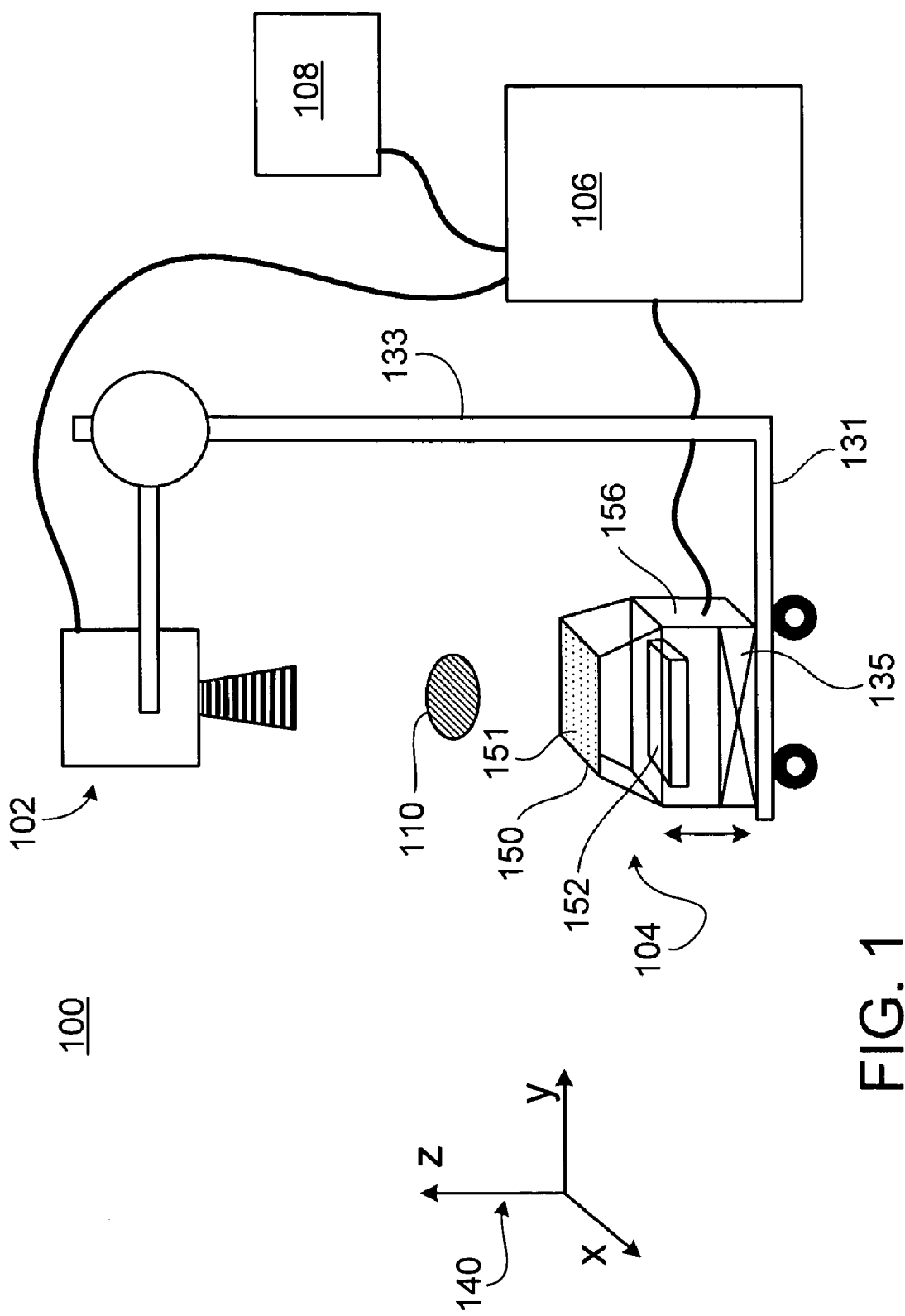
FIG. 1 is a schematic diagram of an imaging system configured to prepare optical and radioscintigraphic images.

Referring to FIG. 1, an imaging system 100 includes an optical imaging system 102, a radioscintigraphic imaging system 104, a processor 106, and a display 108. Optical detection system 102 detects optical radiation from an object 110 and provides at least one optical detector signal indicative of the detected optical radiation. Radioscintigraphic imaging system 104 detects radiation emitted from the object 110, e.g., radiation such as gamma rays emitted by a radionuclide introduced to the object, and provides a radiation detector signal indicative of the detected radiation. Processor 106 can prepare optical image data from the optical detector signal. Processor 106 can prepare radionuclide image data from the radiation detector signal. Processor 106 may alternatively or additionally be configured to prepare image data indicative of a spatial relationship between, e.g., the optical image data and the radionuclide image data.

An exemplary use of instrument 100 is for visualization of an object present within a surgical field, which is typically an area of a subject, e.g., an animal or human patient. In some embodiments, the object 110 includes tissue and/or an organ, e.g., a heart, an intestine, a lymph node, lymph system, a lung, skin, or portion thereof. In some embodiments, the area of the subject is revealed surgically. For example, the area may be a chest opened during a procedure such as a revascularization or cardiac gene therapy, where visualization of the circulatory system may improve identification of areas at risk for myocardial infarction.

In some embodiments, e.g., a sentinel lymph node mapping procedure, the surgical field includes at least one lymph node. The surgical field may include an object such as a tumor that is to be treated or surgically removed. In other embodiments the surgical field is topical, e.g., the skin, or can otherwise be revealed without surgery. Typical surgical fields have a diameter of from about 3 cm to about 25 cm. Working heights, e.g., a distance between an imaged object and the optical imaging system 102 generally range from about 5 cm to about 100 cm.

Typical optical detector signals output by optical imaging system 102 include fluorescence signals, e.g., from a fluorescent compound introduced to the object. Processor 106 can use such optical signals to prepare images that are indicative of the presence and/or distribution of the fluorescent compound within the object. Exemplary fluorescent compounds have a fluorescence maximum in the near-infrared (NIR) and/or infrared (IR) although fluorescent compounds with a maximum in the ultraviolet (UV) or visible may also be used. In some embodiments, the fluorescent compound has an emission maximum between about 780 nm and about 850 nm.

Optical imaging system 102 may alternatively, or in combination, be configured to obtain transmitted and/or reflected light images, e.g., color video, of object 110. For example, in some embodiments, optical detection system 102 provides two detector signals, e.g., a first detector signal indicative of the presence and/or distribution of fluorescence within object 110 and a second detector signal indicative of a reflected light image of the object. Either or both of these optical signals may be video signals, which vary in essentially real-time with changes in the object, e.g., changes in the fluorescence or topography.

The fluorescence optical signals typically provide information related to fine structures, such as the sentinel lymph node location, vessel location, and nerve location. Transmitted and/or reflected light optical signals typically provide information related to the anatomy of the object, such as, e.g., the color and topography thereof. Thus, the combination of reflected and fluorescence light images may provide enhanced information over either image alone.

Exemplary fluorescent compounds, which may also be referred to as fluorescent contrast agents, include polymethines, heptamethine cyanine NIR fluorophores, indocyanine green (ICG), a di-sulfonated indocyanine, and the carboxylic acid form of IRDye78 (IRDye78-CA), a tetra-sulfonated indocyanine that is available as an N-hydroxysuccinimide ester for conjugation to a targeting group, and quantum dots, including an inorganic core, an inorganic shell, and an aqueous solubilizing organic coating to which targeting groups may be conjugated.

The fluorescent compound can be conjugated covalently to small molecules, peptides, and protein targeting molecules. Exemplary fluorescent compounds are described in Frangioni, "In-Vivo Near-Infrared Fluorescence Imaging," Curr. Opin. Chem. Biol., 2003, 7:626-634.

Radioscintigraphic imaging system 104 is generally configured to detect radiation having an energy greater than about 70 keV. In a typical embodiment, a radiation emitter, e.g., a gamma-ray emitting radionuclide, is imaged through a coded aperture mask 150, which is generally an otherwise radioopaque mask that has a series of apertures arranged in a pattern. Each aperture, which may be referred to as a pinhole, forms an image of the object on a detector 152, e.g., a scintillation crystal coupled to a plurality of photon detectors. Detector 152 provides a radiation detector signal that can be processed by processor 106 to prepare an image indicative of the presence and/or distribution of a radionuclide within object 108.

In some embodiments, radioscintigraphic imaging system 104 is configured to detect radiation, e.g., 511 keV gamma rays, resulting from radionuclides typically used in positron emission tomography (PET). These radionuclides include $^{15}$O, $^{13}$N, $^{18}$F, and $^{11}$C. For example, $^{18}$F can be used in the form of 2-[$^{18}$F]fluoro-2-deoxy-D-glucose ($^{18}$FDG), or an $^{18}$FDG linked to a targeting ligand, such as an antibody or other protein or peptide, or a carbohydrate or other moiety that binds specifically to a target, such as a cell surface marker on a tumor (e.g., HER2 on breast cancer cells).

In some embodiments, system 104 is configured to detect radiation from an isotope of thalium, e.g., $^{201}$Tl, technetium, e.g., $^{99M}$Tc, or fluorine, e.g. $^{18}$F. Exemplary technetium containing compounds include, e.g., $^{99M}$Tc-sulfur colloid, $^{99M}$Tc-antimony sulfide, $^{99M}$Tc-nanocolloid, $^{99M}$Tc-methylene diphosphonate (MDP), and $^{99M}$Tc-human serum albumin. Again, these compounds can be linked, e.g., covalently, to a targeting ligand using standard technologies.

Processor 106 can process the detector signals from optical detection system 102 and the radiation detector signal from radioscintographic detection system 104 to prepare multimode image data indicative of the reflected light image of object 110, the presence and/or distribution of the fluorescent compound within the object 110, and the presence and/or distribution of the radionuclide within object 110. The multi-mode image data may be prepared and displayed as a superimposed image including data from all three images.

It is helpful to discuss system 100 with respect to a coordinate system 140. In general, the z-axis of coordinate system is perpendicular to coded aperture mask 150 of system 104. In FIG. 1, the z-axis is aligned vertically and the x-y plane is oriented horizontally. Systems 102, 104 are shown as being aligned along a common axis (the z-axis). System 100, however, is not confined to this configuration. For example, radioscintigraphic imaging system 104 can be rotated so that the z-axis is oriented away from the vertical, e.g., horizontally. In the horizontal radioscintigraphic configuration, systems 102, 104 can be aligned perpendicularly to one another.

Optical Imaging System

Figure 2:
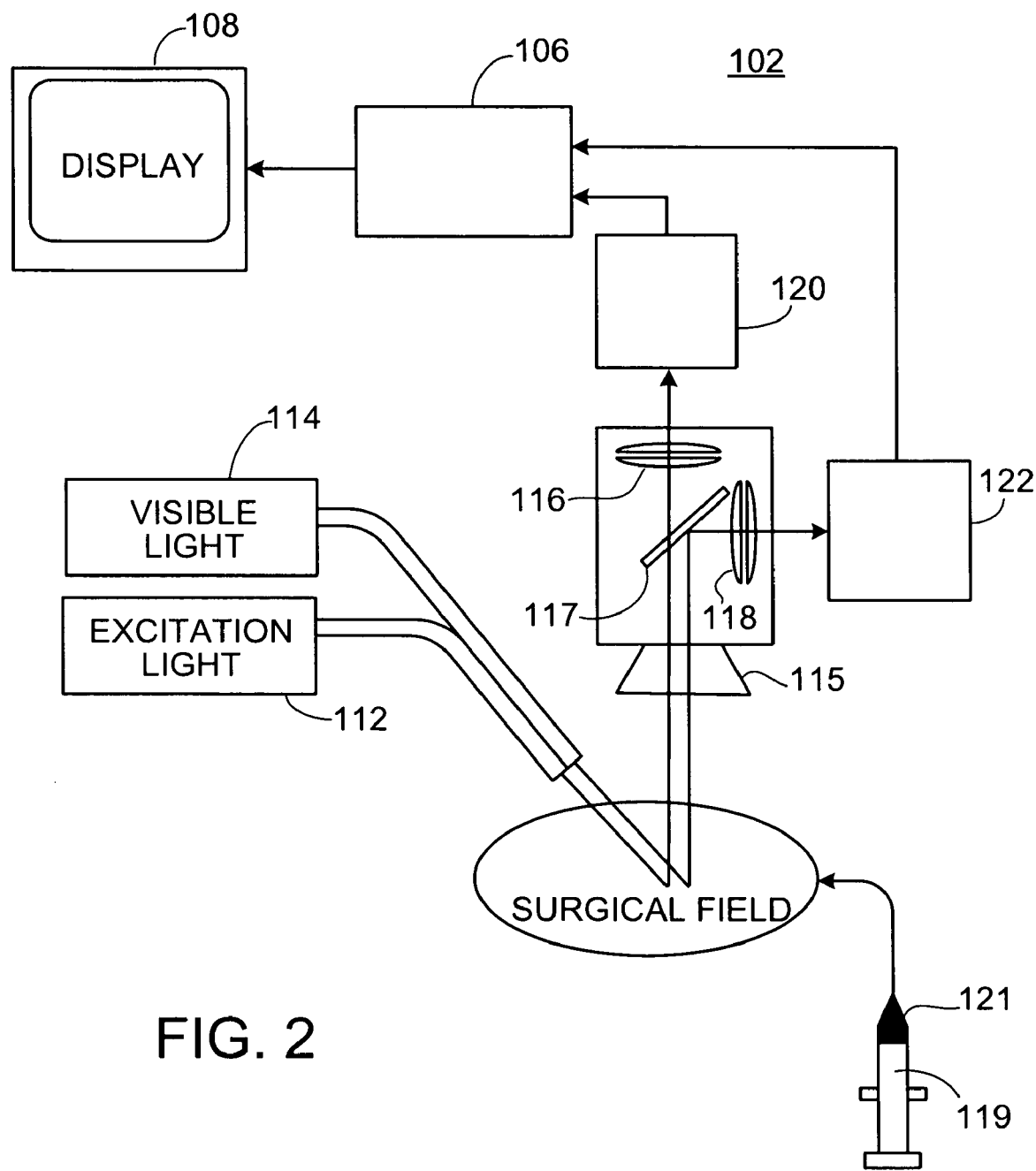
FIG. 2 is a schematic diagram of an optical imaging system of the imaging system of FIG. 1.

Referring to FIG. 2, optical detection system 102 typically includes an excitation light source 112 for exciting fluorescence and may alternatively or in combination include a visible light source 114. Light sources 112, 114 are configured to irradiate an object, e.g., a surgical field or portion thereof, with light. A lens 115 receives fluorescence and/or reflected light from the irradiated object. A first filter 117 directs a portion of the visible light to a first imaging detector 122, which is typically a video camera, e.g., a color video camera, for detecting reflected light. Filter 117 transmits a portion of the light, e.g., fluorescent light, which is received by a second imaging detector 120 configured to detect the fluorescence. The first and second detectors typically view an overlapping portion of the surgical field.

Optical detection systems for obtaining fluorescent and reflected light images of an object are discussed in international application Nos. PCT/US03/16285, filed on May 22, 2003, and PCT/US03/07596, filed on Mar. 11, 2003. See also, De Grand et al., Technol. Cancer Res. Treat., 2:553-562 (2003).

System 102 may also include a fluorescent contrast agent introducer, e.g., a syringe 119, an iv, pump, or other device for introducing an agent 121 into a portion of a human or animal. Typically, the contrast agent is introduced into the bloodstream or directly into a tissue or disease site, e.g., a tumor site.

Upon introduction of the contrast agent, first and second imaging detectors 122, 120 capture one or more images of the surgical field and respectively output first and second optical signals, which are received by processor 106. The first imaging detector generally captures a conventional, visible reflected light image of the surgical field 106. The visible light image includes information about the color, anatomy, and/or topography of the object. The second imaging detector generally detects a diagnostic image indicative of the distribution of the fluorescent contrast agent in the surgical field. The processor prepares image data from the optical signals. The prepared image data typically combine information from both optical signals. The combined image data may be presented on display 108 where, for example, a user, such as a surgeon, may view the images.

Imaging system 100 may be used within an operating area (not shown), which is closed to ambient light. As will become clear from the following, many visible light sources such as incandescent lamps, halogen lamps, or daylight may include a broad spectrum of electromagnetic radiation that extends beyond the range of visible light detected by the human eye and into NIR and IR wavelengths that are typically detected by system 102. To effectively detect emission in these super-visible light wavelengths, in surgical field 106, light sources 112, 114, and detectors 120, 122 are generally enclosed in an area that is not exposed to broadband light sources. This may be achieved by using an operating room closed to external light sources, or by using a hood or other enclosure or covering for the surgical field 106 that prevents invasion by unwanted light. The visible light source 102 may then serve as a light source for the visible light camera 122, and also for conventional lighting within the visible light spectrum. Thus, system 100 may be used to view a surgical site or other object that is protected from sunlight and/or other ambient light.

Visible light source 114 is typically a near-infrared depleted white light source, e.g., a one-hundred fifty Watt halogen lamp (e.g., 0.5 mW/cm$^2$) with one or more filters to attenuate emission at wavelengths greater than 700 nanometers (nm). Generally, any light source emitting wavelengths between 400 nm and 700 mm may serve as the visible light source. In some embodiments, the light source 114 is a 100 W metal halide light source (Dolan-Jenner model MH-100), which emits NIR-depleted visible light. The blue emission from the metal halide source compensates for the relatively low blue sensitivities of certain detectors, thereby providing more faithful color reproduction of the surgical field.

The visible light source may be provided with a digitally controlled on/off function and/or an iris that may be used to reduce the amount of light illuminating the surgical field. The on/off function and iris are typically under control of processor 106.

Suitable optical coupling and lenses may be provided to direct each of the visible light source 102 and the excitation light source 104 at an area of interest within the surgical field 106. An adjustable focus ring light (Photonics, Inc., Austria) may be used to deliver visible light, e.g., NIR-depleted light to the surgical field. Exemplary ring lights have a working distance about the same as that of the lens, e.g., a working distance of 12-18" and deliver homogenous white light over the surgical field. The light may also be introduced to the surgical field via a ¼" fiber optic bundle.

In some embodiments, the excitation light source 112 and resulting emission from the contrast agent 121 may emit wavelengths near or below 700 nm, as with Cy5 dye, which emits light when excited at 650 nm. Such near-red dyes may be used with system 102. Typically, visible light source 114 is turned off during acquisition of fluorescence at these wavelengths. Alternatively, a visible light source that excludes a portion of the visible light spectrum in which the contrast agent emits, e.g., a far-red depleted white light source may be used. In general, it is preferred that the visible light source does not emit substantial amounts of light at wavelengths at which fluorescence will be detected. Thus, in general, the visible light source 114 is a source of light that includes some, but not necessarily all, of the wavelengths of visible light.

Excitation light source 112 emits light at a wavelength that excites fluorescence from the fluorescent contrast agent 121. In some embodiments, the light source 112 outputs light having a wavelength in the far-red, e.g., from about 650 nm to about 800 nm, NIR, e.g., from about 700 nm to about 1000 nm (e.g., about 725-755 nm), IR, e.g., from about 1000 nm to about 3000 nm, or combination thereof. The light source may be broadband or narrow band. In some embodiments, the light source 112 is a diode, e.g., a laser diode such as a 771 nm, 250 mW laser diode system, which may be obtained from Laser Components of Santa Rosa, Calif. A plurality of light emitting diodes, e.g., diodes emitting light of from about 725 nm to about 775 nm, may also be used. An exemplary excitation light source 112 provides an excitation light fluence of up to about 5 mW/cm$^2$ over a 15 to 20 cm diameter surgical field.

Lens 115 is configured to receive light (generally including both visible and fluorescent light) from the surgical field 106 and focus the light for image capture by the first and second imaging detectors. Lens 115 may include one or more optical coatings suitable for the wavelengths to be imaged, and may be provided with manual, electronically-assisted manual, or automatic control of zoom and focus. In some embodiments, the focus and zoom is automated and under control of processor 106 in conjunction with an algorithm, described below, for registering images provided by the radionuclide imaging system 104 and optical imaging system 102.

Filter 117 is generally configured to separate fluorescence emitted by the fluorescent contrast agent from visible light detected by the first imaging detector. For example, filter 117 is generally positioned in the image path from the lens 115 such that a visible light image having one or more visible light wavelengths is directed toward the detector 122, either by reflection or transmittance. A fluorescence image from the excited contrast agent passes through the lens 115 and is directed toward the detector 120, again either through reflection or transmittance. A number of arrangements of the detectors 120, 122 and the first filter 117 are possible, and may involving reflecting or transmitting either the visible light image or the emission wavelength image. In some embodiments, filter 117 is a Nikon TE-300 filter cube (in the inverted position), which includes a dichroic mirror, NIR emission filter (790-830 nm) and a color video camera filter (400-700 nm).

In general, first and second imaging detectors 122, 120 may be any devices capable of detecting light and providing a signal that may be converted to prepare image data. Typical detectors include linear photodiode arrays, charge coupled device arrays, scanning photomultiplier tubes, and so forth.

First imaging detector 122 is generally any detector suitable for capturing images, e.g., video images, of the surgical field 106 in the visible light spectrum. In some embodiments, the first imaging detector is a color video camera model HV-D27, available from Hitachi of Tarrytown, N.Y. The first imaging detector may capture red-green-blue (RGB) images at thirty frames per second at a resolution of 640×480 pixels.

Second imaging detector 120 is configured to detect fluorescence from a selected fluorescence compound. Typical imaging detectors can detect light in the far-red wavelength range, NIR, IR, or combination thereof. Imaging detectors sensitive to far-red, near-infrared, and infrared wavelengths are commercially available. In some embodiments, the second imaging detector is an Orca-ER® near-infrared camera with a 640×480 pixel field of view, an exposure time of 67 msec, and an effective frame rate of fifteen frames per second. The OrcaER® is available from Hamamatsu Photonic Systems of Bridgewater, N.J.

The first and/or second detectors may be configured to reduce or prevent noise caused by operation in proximity with radiation, e.g., gamma rays, emitted by radionuclides that may be used in conjunction with system 100. For example, the Orca-AG® NIR CCD detector can detect scintillations (which appear as detector noise) when the camera is focused on a 1 mCi source at a working distance of 12". To reduce the scintillations, the geometry of the detector is modified so that shielding, e.g., lead antimony shielding, can be positioned intermediate the detector and radiation source. In some embodiments, a NIR reflecting mirror, e.g., a gold mirror, is positioned to reflect fluorescence into the detector, which is mounted on its side. Lead antimony shielding is placed between the radioactive source and the CCD elements of the detector with only a small increase in optical imaging system weight. Typically, processor 106 rotates the optical signals to account for the different detector orientation. Other detectors, e.g., the Hitachi HV-D27® color CCD camera, are more robust with respect to scintillations and may be used without shielding up to 120 mCi of 99 mTc at a distance of 2".

In some embodiments, system 100 is used with the fluorescent contrast agent IRDye78-CA (carboxylic acid), which has a peak absorption near 771 nm and a peak fluorescence emission near 806 nm. In such embodiments, the first filter 117 can be a 785 nm dichroic mirror that transmits near-infrared light and reflects visible light. The first filter 117 may be positioned along an image path from the lens 117 such that a visible light image of the surgical field is reflected toward the detector 122 through a third filter 118. The third filter 118 can be, for example, a 400 nm-700 nm visible light filter. First filter 114 transmits a near-infrared fluorescence image toward detector 120 a second filter 116. The second filter 116 can be an 810 nm +/−20 nm near-infrared emission filter. The filters may be standard or custom-ordered optical components, which are commercially available from optical component suppliers. Other arrangements of filters and other optical components cam be used with the system 100 described herein.

Display 108 is typically a television, high-definition television, computer monitor, or other display configured to receive and render signals from the processor 106. In some embodiments, e.g., in which the surgical field is a neurosurgical site, a surgical microscope can be used to view the surgical field 106. Display 108 may present images to an operator via a monocular or binocular eyepiece of the surgical microscope, with the near-infrared image superimposed on the visible light image in the eyepiece. The eyepiece may alternatively or in combination use direct optical coupling of the surgical field to the eyepiece for conventional microscopic viewing, with the near-infrared image projected onto the eyepiece using, for example, heads-up display technology.

Processor 106 includes software and/or hardware suitable for receiving images and/or detector signals from the detectors, processing the images and signals as desired, and transmitting image data to the display. In general, any processor e.g., a computer, may be programmed to perform the image processing functions described herein, including an Intel® processor-based computer, a PC, or a computer using hardware from Sun Microsystems®, Silicon Graphics, or any other microprocessor manufacturer. In one embodiment, the processor is a PC equipped with a PCI-1422® frame grabber from National Instruments or a Macintosh® computer equipped with a Digi-16 Snapper® frame grabber for the Orca-ER®, commercially available from Data Cell of North Billerica, Mass., or a PC equipped with a PCI-1411® frame grabber for the HV-D27®, commercially available from National Instruments, and using LabView® software, commercially available from Scanalytics® of Fairfax, Va.

Processor 106 is typically configured to perform functions such as digital filtering, gain adjustment, color balancing, and other image processing functions. Processor 106 can also prepare pseudo color images from fluorescent (and radioscintographic) data for display at some prominent wavelength, e.g., a color distinct from the visible light colors of the surgical field 106, so that a superimposed image will be discernible to an operator. Processor 106 may also perform image processing to combine the image from the near-infrared camera 120 and the video camera 122.

In some embodiments, the reflected light and fluorescence images are displayed in different locations on the display. In some embodiments, the images are superimposed. Processor 106 can be configured to adjust the frame rate of images acquired using different detectors or modalities. For example, the first detector may capture data images at a rate of thirty frames per second and the second detector may capture data at an effective frame rate of fifteen frames per second. Processor 106 can reduce the frame rate of the first detector, such as by using every other frame of reflected light data or averaging or otherwise interpolating video data to a slower frame rate. Processor 106 can instead or additionally increase the frame rate of the near-infrared image data, either by holding each frame of fluorescence data over successive frames of reflected light data or extrapolating fluorescence data, such as by warping the fluorescence image according to changes in the reflected light image or employing other image processing techniques.

Functional aspects of processor 106 are typically realized in one or more microprocessors, microcontrollers, embedded microcontrollers, programmable digital signal processors or other programmable devices, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The functions may also, or instead, include one or more application specific integrated circuits, programmable gate arrays, programmable array logic devices, or any other device or devices that may be configured to process electronic signals. Any combination of the above circuits and components, whether packaged discretely, as a chip, as a chipset, or as a die, may be suitably adapted to use with the systems described herein.

Processor 106 can include or operate with a computer readable medium configured with executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. Processor 106 can be deployed using software technologies or development environments including a mix of software languages.

Radioscintigraphic Imaging System

Returning to FIG. 1, radioscintigraphic imaging system 104 is a coded aperture detection system in which coded aperture mask 150 receives radiation emitted by radionuclides present within object 110. Each aperture 151 transmits radiation to detector 152 while non-aperture portions of mask 150 obstruct or attenuate the amount of radiation reaching detector 152. Each aperture 151 typically forms an image on detector 152 of each radioactive point within the imaged object. Because there are many imaged points and many apertures, detector 152 receives radiation corresponding to a plurality of generally overlapped images of the object.

Detector 152 typically includes a scintillation crystal that emits light when irradiated with radiation and a plurality of light detectors to detect the scintillations. In some embodiments, the detector 152 is an Anger camera that has been modified to remove collimating structures within the camera. An exemplary detector is a slim-line Park Medical Isocam II® camera head (Northern Nuclear). This camera head is about 10" high, permitting all electronics to reside more than about 6 feet from the operating room table. The slim-line Isocam II maximizes clearance between the bottom of the operating table and the scintillation crystal, which will lie about 12 inches off the floor in some configurations.

In some embodiments, detector 152 includes one or more pixilated arrays of cadmium-zinc-telluride (CZT) semiconductor detectors. The CZT material is a room temperature semiconductor and exhibits a high absorption efficiency from 10 keV to 1 MeV. A CZT detector has better energy resolution by several % and better spatial resolution (<100 µm) than scintillation crystals.

In some embodiments, detector 152 includes one or more, e.g., four, microsphere plate (MSP) multipliers. Suitable MSP multipliers are available from Nova Scientific (Sturbridge, Mass.). Typical MSP multipliers include a photocathode which emits photoelectrons when struck by visible photons from scintillators and a thin layer of glass spheres made from a glass that emits electrons when struck by the photoelectrons. The electrons drift through the plate and, by secondary emission, produce electron gain. In effect, the entire plate acts as a position sensitive photomultiplier tube (PMT) but without the complex internal structure of PMTs. A voltage of a few kV accelerates the photoelectrons, which can be detected by an electrode structure deposited on the rear of the MSP.

In some embodiments, the detector includes a microchannel plate (MCP). An MCP is a secondary-electron multiplier which detects and amplifies electrons in two-dimensions. MCP's are sensitive not only to electrons but to ions, vacuum ultraviolet light, X-rays, and Gamma-rays.

We use the term MSP to denote either a bare MSP or a combination of a photocathode-MSP which converts visible light to electrons.

In use, a scintillation crystal is located adjacent to or in contact with an MSP multiplier so that the multiplier can detect scintillations caused by gamma rays that pass through a coded aperture mask and strike the crystal. Readout electrodes of the MSP are positioned away from the crystal so as not to obstruct photons produced by the crystal. Typically, a 2.5 cm thick scintillation crystal is used. Spatial resolution is approximately 100 µm. The efficiency for $^{99m}$Tc is at least that of a conventional Anger camera.

In a typical configuration, four MSP coded aperture detectors are symmetrically arranged around optical system 102 so that each MSP detector and the optical system have overlapping fields of view. The MSP coded aperture detectors and optical system typically view the imaged object from the same side of the object. The same-side-of-the-object orientation allows the optical and radiation imaging systems to be simultaneously and rapidly positioned over a surgical field.

Because the different MSP detectors have slightly different orientations with respect to the field of view, additional tomographic information is obtained as compared to a single radiation detector system. The field of view, magnification, and intrinsic system resolution of such systems are generally about 15 cm, 1.5 and 1 mm, respectively.

A distance between the mask 150 and the scintillation crystal of detector 152 can be adjusted to vary the field of view and magnification of the system. A typical maximum crystal-to-mask distance is about 65 cm. The Isocam detector has an intrinsic full-width half-maximum resolution (FWHM) of 2.7 mm for $^{99m}$Tc. The Isocam detector has a field of view that is greater than the field of view of the mask 150, which avoids edge effects. The system can be positioned to image any horizontal plane within a 15×15 cm field of view extending from the tabletop to a height of 30 cm above the tabletop.

The radioscintigraphic imaging system can be configured to acquire radiation detector data along any orientation with respect to an object. In some embodiments, the system 104 is configured to acquire radiation detector data along substantially the same axis as system 102 acquires optical detector data. This axis can be a substantially vertical axis and the systems can be configured to acquire the optical and radiation data from above the object.

Processor 106 receives and processes the detector signal to prepare a single image of the object from the plurality of detected object images. Typical algorithms to prepare an image from the detector signal include one or more deconvolution steps as described in the papers Accorsi et al., "A Coded Aperture For High-Resolution Nuclear Medicine Planar Imaging With A Conventional Anger Camera: Experimental Results," IEEE Trans. Nucl. Sci., 2001, 48:2411-2417; and Accorsi et al., "Optimal Coded Aperture Patterns For Improved SNR in Nuclear Medicine Imaging," Nucl. Instr. Methods Phys. Res. A, 2001, 474:273-284.

i. Coded Aperture Masks

Mask 150 includes a substrate having an array of at least about 500 apertures, e.g., at least 1,000 apertures, or even as many as 5,000 apertures, or more. In some embodiments, the apertures are holes in the substrate. In other embodiments, the apertures are not holes extending through the substrate, but comprise regions that are more transparent with respect to radiation than the substrate of the mask. For example, the apertures may be thinned areas comprising the same material as the substrate of the mask. The apertures may be holes in the substrate that are filled with a material that transmits most of the radiation. In any event, apertures of the mask may transmit most or essentially all of the radiation striking (or passing through) the apertures. Accordingly, the apertures may be referred to as transparent portions. Non-aperture regions of the mask, e.g., the substrate, generally block a substantially higher amount of radiation than the apertures such as at least about 70%, at least about 80%, e.g., at least about 95% percent of radiation striking the non-aperture regions. In general, each aperture has a diameter of from about 0.5 mm to about 3 mm. The amount of radiation blocked depends upon the thickness of mask 150, the material used to prepare mask 150, and the energy of the radiation.

In some embodiments, coded aperture mask 150 includes tungsten. Exemplary masks have a tungsten content of at least about 80%, a density of at least about 15 g/cm$^3$, a hardness of at least about 20 Rc, a tensile strength of at least about 80,000 psi, and a low thermal expansion coefficient. In some embodiments the tungsten alloy K1750® (Kulite Tungsten, Inc.) is used to form the mask. This alloy includes 92.5% tungsten, has a density of 17.5 g/cm$^3$, a hardness of 24 Rc, and a tensile strength of 110,000 psi. The K1750 alloy can be obtained in sheets of varying thickness. The alloy can be manipulated, without cracking or gumming, using high speed circuit board drills allowing rapid manufacture of masks having, e.g., over 8,000 apertures. In general, the apertures 151 are round cylinders, e.g., one penetration of a standard drill bit, although other shapes, e.g., square may be used.

Mask thickness depends on the energy of the imaged radionuclide and the amount of attenuation required. A 3.96 mm thick K1750 alloy mask may block about 70% of radiation having an energy of 511 keV and a 0.99 mm mask will block about 93% of radiation having an energy of about 140 keV.

In some cases, however, a thicker mask may be desired. Masks of increased thickness can be provided by, for example, combining sheets of material by stacking, bending, and forming apertures as a single unit. Another suitable tungsten alloy, Densalloy® (MI Tech Metals), has physical characteristics similar to K1750 and can be purchased as a block that can be shaved using standard electrocautery techniques, thus achieving any desired mask thickness.

The size of the apertures 151 determines to a certain extent the final spatial resolution of reconstructed images. In some embodiments, such as for intraoperative applications, where higher resolution sufficient to locate sentinel lymph nodes is beneficial, a slightly thinner mask with correspondingly smaller apertures is used. In some embodiments, the mask has dimensions of 26.5 cm per side, is about 0.99 mm thick, and includes 8987 holes of 0.994 mm diameter. Such a mask provides a field of view in the x-y plane (parallel to the plane of the mask) of 15 cm×15 cm and a depth of field of 30 cm along the z-axis (perpendicular to the mask). The geometric resolution is 1.49 mm in the x-y plane and 11.9 mm along the z-axis. The system resolution is 1.94 mm in the x-y plane and 15.5 mm along the z-axis. The magnification is about 3.7.

Typically, the apertures are arranged in a no-two-holes-touching (NTHT) pattern or a modified uniformly redundant array (MURA) pattern. See, e.g., Accorsi et al., "A Coded Aperture For High-Resolution Nuclear Medicine Planar Imaging With A Conventional Anger Camera: Experimental Results," IEEE Trans. Nucl. Sci., 2001, 48:2411-2417; and Accorsi et al., "Optimal Coded Aperture patterns for improved SNR in Nuclear Medicine imaging, "Nucl. Instr. Methods Phys. Res. A, 2001, 474:273-284.

The mask is secured to a frame 156, e.g., an aluminum frame, which in is coupled to the detector 152 generally without a collimator. The frame 156 is typically shielded, e.g., with 6 mm lead antimony, at a thickness yielding>99.9% attenuation for $^{99m}$Tc, allowing masks to be interchanged without having to change camera shielding.

In some embodiments, the optical and radioscintigraphic imaging sub-systems are mounted on a mobile cart 131 (Pucell Enterprises, Cleveland, Ohio). The cart includes a bottom platform mounted on a low-profile, 40"×22" scissor lift 135. The slim-line Isocam II camera head, secured within the frame, sits on a scissor lift platform and can be rotated from a "facing up" configuration (in which the z-axis of the mask is vertical) to a "facing in" position (in which the z-axis of the mask is horizontal) via an independent set of hydraulics.

Mounted rigidly to the cart is a double-slotted aluminum extrusion beam 133. The optical system 102 is positionable along the beam 133 for coarse adjustment of its height relative to the radioscintigraphic system 104. Further z-adjustment of the optical sub-system, especially during system co-registration, is via a stepper motor under control of processor 106.

ii. Radioscintigraphic Image Reconstruction

Processor 106 typically prepares radioscintigraphic images by Fourier deconvolution of data output by radioscintigraphic system 104. Radioscintigraphic image processing is discussed in the paper Schellingerhout et al., Coded Aperture Nuclear Scintigraphy: A Novel Small Animal Imaging Technique. Molecular Imaging, 2002, 1:344-353. Using, for example, the 8987 aperture mask discussed above, system 104 provides radioscintigraphic images having a FWHM of 1.94 mm in the x-y plane parallel to coded aperture mask 150 and a FWHM resolution of 15.5 mm along the z-axis perpendicular to the mask 150.

In medical applications of system 100, the object is typically imaged in a near-field configuration. This differs from other applications of coded aperture imaging in which objects are imaged in a far-field configuration. When a distant object is imaged using a coded aperture detection system, all gamma rays originating from the same point within the object reach the coded aperture mask with the same incidence angle (far-field geometry). When a near-field object is imaged, as in medical imaging applications, gamma rays originating from the same point within the object reach the coded aperture mask with different incidence angles (near-field geometry). In the absence of corrective processing, the different incidence angles of the gamma rays can create artifacts in images reconstructed from the detector signal.

Processor 106 is generally configured to prepare radiation images that have been corrected for near-field errors. In some embodiments, the algorithm for correcting near-field errors requires acquiring first radiation detector data with the coded aperture in a first orientation and second radiation detector data with the coded aperture mask in a different orientation, e.g., rotated 90° about the z-axis of the mask. Processor 106 uses the first and second radiation detector data to correct images prepared from the data for near-field errors. Correction for near-field errors is discussed in Accorsi, R. and R. C. Lanza, Near-Field Artifact Reduction In Coded Aperture Imaging, Applied Optics, 2001, 40:4697-4705, and U.S. Pat. No. 6,737,652, issued on May 18, 2004.

In some embodiments, the imaged object includes radionuclide distributed at a plurality of distances along the z-axis with respect to the coded aperture mask 150. The radiation detector 152 typically detects radiation from the radionuclide located at a plurality of the z-axis locations. Processor 106 can generate radioscintigraphic image slices corresponding to a selected distance from the coded aperture mask along the z-axis. The process is based upon differences in the detector signal obtained from points at different z-axis locations.

As discussed above, the apertures 151 of mask 150 form an image of each radioactive point in the imaged object. The image size for each point decreases for points more distant from mask 150. Image slices corresponding to a particular plane along and generally perpendicular to the z-axis can be prepared selecting parameters of the deconvolution function to correspond with the size of the image created by points within the object at the selected z-axis distance. Advantageously, two-dimensional slices corresponding to a plurality of z-axis distances can be prepared from a single radiation detector signal. The slices can be assembled along the z-axis to provide tomographic (three-dimensional) data, which may contain, e.g., at least 5, 10, 20, or even 40 slices. This tomographic imaging technique has been called "laminography."

The stack of slices can be filtered along a dimension extending through the stack of slices to improve resolution along the z-axis perpendicular to the coded aperture mask. This filtering step is typically accomplished using in the Fourier domain using a filtering function derived from the inverse of the point spread function of the coded aperture mask.

Typically, the Fourier deconvolution of a given plane is independent of other planes. The Fourier reconstruction of a single plane takes only 900 msec using a single 3.1 GHz Pentium 4 machine. A stack of 40 planes can be reconstructed simultaneously in 900 msec by a parallel processor comprising 40 CPU's, and the entire reconstruction process, including Fourier filtering and display, can be accomplished in less than 5 seconds. Thus, three-dimensional radioscintigraphic images can be acquired and displayed in near real-time.

For typical coded aperture imaging systems, resolution along the z-axis (the direction perpendicular to the plane of the coded aperture mask) is approximately eight times worse than the resolution within the x-y plane (the plane parallel to the plane of the coded aperture mask). As discussed above, system 100 allows an operator to rotate the z-axis of the coded aperture mask between horizontal and vertical orientations. In a horizontal z-axis orientation, the improved x-y plane is parallel to the optical axis of the optical imaging system 102. This configuration can provide radioscintigraphic images with improved depth resolution into a horizontally situated object, e.g., a patient on a horizontal support. In general, system 104 may be rotated to bring the higher radioscintigraphic resolution into any plane.

With the coded aperture positioned beneath an object with the z-axis in a vertical orientation, attenuation of gamma rays by the tissue may occur. For example, the radiation from $^{99m}$Tc (140 keV, $\mu$=0.15 cm$^{-1}$) has a narrow beam transmission value of 0.472, 0.223, 0.105, 0.05, and 0.024 through 5, 10, 15, 20, and 25 cm of tissue, respectively. For superficial procedures with the detector in the vertical configuration, the radioscintigraphy system will receive radiation that has penetrated almost the entire thickness of the subject. Deeper structures are less affected by attenuation than the more anterior structures for a detector placed beneath the imaged subject.

In the case of complementary dual-mode imaging, the relative increase in activity on the opposite side of the subject can be advantageous. The activity can alert the surgeon to deep lesions, which may not have originally been targeted for resection. For example, it is not uncommon in lymphoscintigraphy on the upper back to have draining nodes in the supraclavicular fossa. These nodes could be undetected with the NIR imaging, but the radioscintigraphy would be exquisitely sensitive to tumors in these locations.

In many circumstances the losses due to attenuation in the "facing up" position will be sizable. However, the high sensitivity of the coded aperture system will tend to ameliorate these losses, at least as compared to other nuclear medicine imagers. For example, the count rate in the coded aperture system with 480 holes for a point source at 10 cm is 440 times the count rate through a single pinhole. The gain in sensitivity is less than the number of holes due to geometrical factors and varies with the depth of the point source. For a $^{99m}$Tc point source on the far side of a patient who is 25 cm thick, the sensitivity of the coded aperture system from below the table is 10.3 times greater (440×0.023) than routine pinhole imaging from above the table. In the case of a point source, the signal-to-noise ratio is directly related to the count rate. For some SLN surgeries, the horizontal z-axis coded aperture mask configuration can be advantageous.

In some embodiments, resolution along the z-axis with respect to the coded aperture mask 150 is enhanced by an iterative image reconstruction process. The method typically includes obtaining a radiation detector signal using coded aperture mask 150, providing an initial estimate of the distribution (activity) of radionuclide within the imaged object, and using the initial estimate in an iterative process to obtain increasingly well-resolved images of the object. The iterative algorithm also corrects for near-field errors. Thus, radioscintigraphic images corrected for near-field errors can be prepared without the acquisition of a second radiation detector signal with the coded aperture mask rotated about the z-axis. The algorithm is discussed next with reference to a three-dimensional representation of an object.

Figure 3:
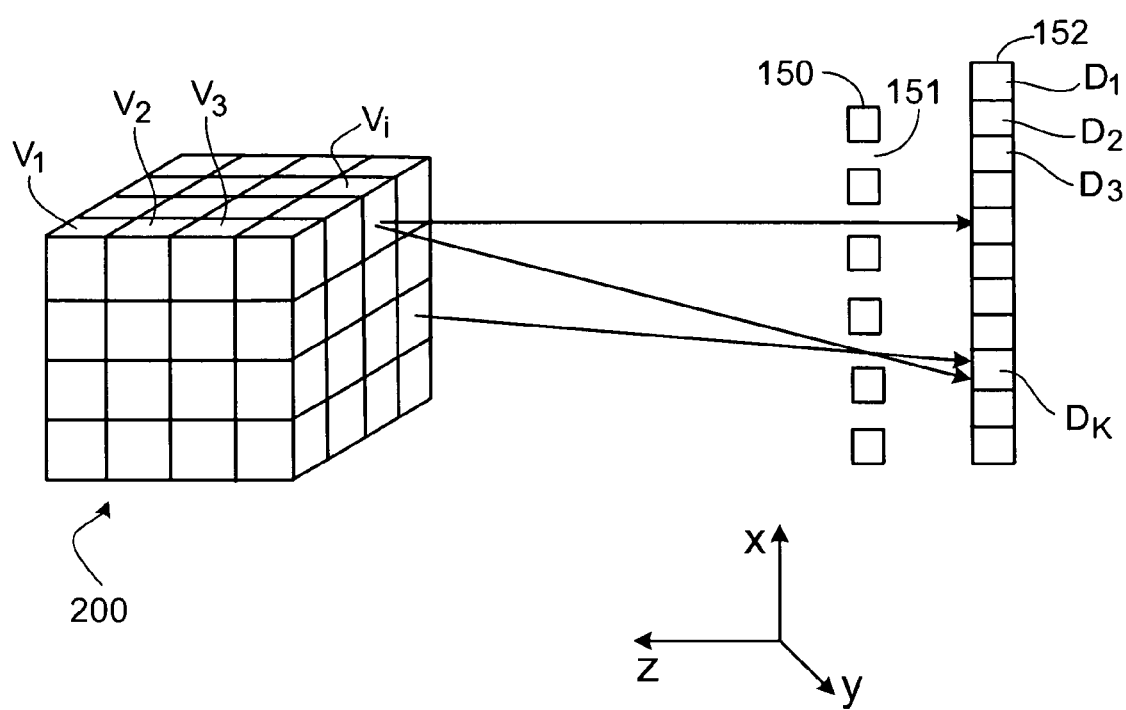
FIG. 3 is a schematic diagram that illustrates detection of radiation through a coded aperture mask.

Referring to FIG. 3, an imaged object 200 can be represented in three dimensions as a plurality of voxels V, where $V_i$ is the ith voxel. The intensity of the radionuclide activity in the ith voxel is $O_i$. A portion of the radiation emitted by radionuclide within each voxel impinges upon detector 152, which includes a plurality of detector elements $D_k$. The predicted detector signal, $I_k$, from the kth detector element is given by:

$$I_k = \sum_i P_{ik} O_i \qquad (1)$$

where $P_{ik}$ is an element of a probability matrix $P_{ik}$, contains a number N entries, where N equals the product of the number of voxels and the number of detector elements. Each entry describes, for a particular voxel-detector element pair, the probability that a gamma ray emitted from within the voxel will impinge upon and be detected at the detector element. Thus, $P_{ik}$ represents the probability that a photon emitted in the $i^{th}$ voxel will be detected in the $k^{th}$ detector element. The elements $P_{ik}$ may be expressed as a product of factors representing the physics of the detection process. These factors include (but are not limited to) the transmission (T) of radiation due to the pattern of pinholes in the coded aperture mask, the penetration (P) of radiation through the mask wall (the non-aperture portions of the face of the mask), a geometric factor (G), the detector efficiency and resolution (D), and the dependence of the transmission of radiation through the pinholes on the angle of incidence due to the finite thickness of the mask (C).

The probability matrix can be large. A typical coarse resolution of a cube 15 cm long per side using 0.5 cm voxels requires $30^3$ voxels. Detector 152 typically includes an array of $512^2$ detector elements. Thus, even for a coarse resolution, the probability matrix may contain $30^3 \times 512^2 = 7 \times 10^9$ entries. The probability matrix, $P_{ik}$, which depends on geometry, absorption in the patient and the coded aperture mask, the detector efficiency, and the detector resolution and may be computed in advance and stored for use during reconstruction or computed as needed by processor 106. Generally, the probability matrix is read into memory during each iteration because single desktop computers cannot hold the entire matrix at once.

A typical iterative algorithm is the Ordered Subsets Expectation Maximization (OSEM) algorithm. Each iteration improves the tomographic reconstruction of an imaged object. Initially, the expected detector data $I_k(\exp)$ can be generated from a theoretical estimate of voxel activities or from an estimate of voxel activities derived from actual radiation detector data.

An initial estimate of the expected detector data $I_k(\exp)$ can be generated from a theoretical estimate of voxel activities by assuming an even distribution of radionuclide activity within the voxels of the object and using the probability matrix $P_{ik}$ and Eq. 1 to project the activities onto the detector.

An initial estimate of the expected detector data $I_k(\exp)$ can be generated from actual radiation detector data by acquiring radiation detector data from the object and subjecting the data to laminography to provide, for each plane of voxels within the object, an estimate of radionuclide activity. These estimated radionuclide activities are projected onto the detector to using the probability matrix $P_{ik}$ and Eq. 1.

Processor 106 computes the (n+1)th estimate of the voxel activities using a weighted average:

$$O_{i(n+1)} = O_{i(n)} \sum_k \left( \frac{P_{ik}}{\sum_k P_{ik}} \right) \left( \frac{I_{k(obs)}}{I_{k(\exp)}} \right) \quad (2)$$

where $O_{i(n+1)}$ is the activity estimated from the (n+1)th iteration and $O_{i(n)}$ is the activity estimated from the nth iteration. The determination of Eq. 2 is performed for each voxel. The algorithm generally proceeds until the change during a single iteration in the sum of the squares of the differences between I(exp) and I(obs) reaches a predetermined minimum.

Upon completion of the algorithm, the estimated activities for the voxels $O_i$, can be used to prepare radioscintigraphic images comprising any or all of the voxels. For example, one or more radioscintigraphic image slices, each comprising the voxels of a particular plane within the object, can be prepared. Thus, using a coded aperture mask to obtain radiation detector data, and subjecting the data to the iterative process, one can obtain tomographic radioscintigraphic images of an object without the requirement for moving the mask or the acquisition of a plurality of detector signals. The single detector signal is typically acquired along a single detection axis.

In some embodiments, processor 206 is configured to reduce the size of the probability matrix thereby increasing the speed at which processor 206 can iteratively prepare radioscintigraphic images. A point source of radiation in a single object voxel will cast a shadow of the mask onto the detector which reflects all of the factors T, P, G, D, C referred to above. The computation of the probabilities $P_{ik}$ is greatly accelerated by recognizing that these the functions T, P, G, D, C can be treated as identical in form for every object voxel in an object plane parallel to the mask (the x-y plane), differing only by their center on the detector as we move from one object voxel to another. For example, the transmission function (T) reflecting the pattern of pinholes will be centered at the point on the detector where a ray from the object voxel through the center of the mask strikes the detector. All of the other functions will be centered on the detector at a point where the perpendicular projection from the object voxel strikes the detector and will depend only on the azimuthal angle (θ) between the z-direction and a line connecting the object voxel to the detector element. For example, the maximum probability for penetration both through apertures of the mask (C) and through the non-aperture portions of the mask (P) occurs for radiation traveling perpendicular to the mask (parallel to the z-axis) with θ=0.

We may therefore, express the probabilities $P_{ik}$ as a product of just two functions $$P_{ik} = (T) * (PGDC) \quad (3)$$

which are centered at different locations on the detector. Only for the object voxel at the center of the plane will (T) and (PGDC) share a common origin, or center. Both of these functions are defined for each of the $512^2$ detector elements. However, since T and PGDC are identical in form for every object voxel in a particular plane, we need only shift these functions to their respective centers and multiply them to generate an entire plane of probabilities. The entire probability matrix can then be constructed quickly using only two matrices of $512^2$ elements for each plane in the object. This greatly speeds the real-time computation of the probability matrix and reduces the enormous I/O burden associated with pre-computing the probabilities and storing them on disk, as described above.

Figure 4A:
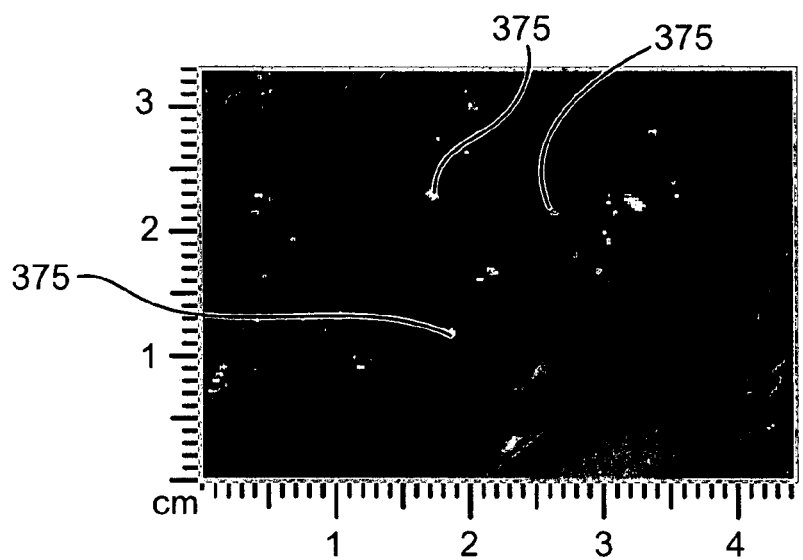
FIG. 4a is a top-view simulated merged image that includes reflected light optical image data of tissue and radioscintigraphic image data of three anion exchange resin beads doped with a technetium isotope.
Figure 4B:
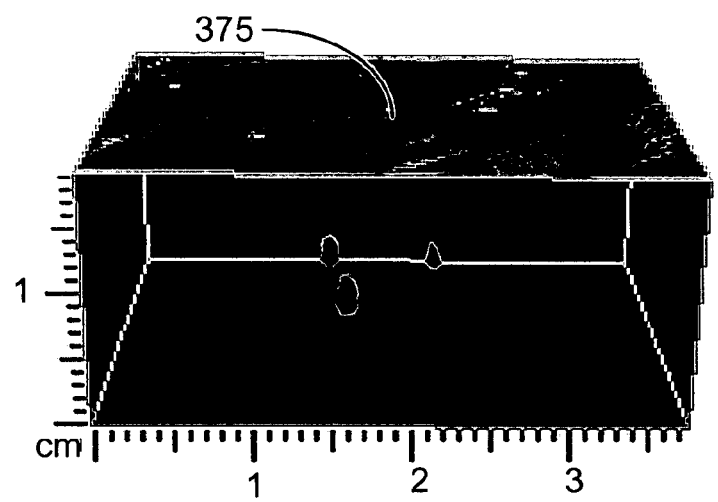
FIG. 4b is a perspective side view of the tissue and beads of FIG. 4a illustrating a distance between the location of the tissue surface and the beads therebelow.
Figure 4C:
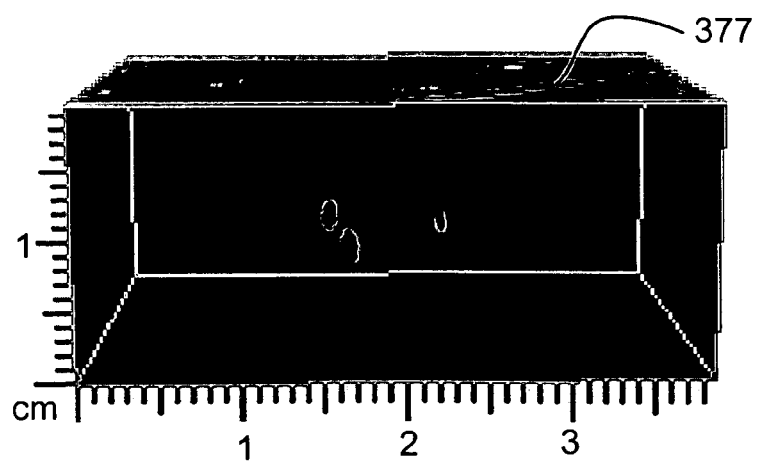

Referring to FIGS. 4*a*-4*c*, the iterative algorithm successfully reconstructs tomographic images from a single radiation detector signal. Each of the images in FIGS. 4*a*-4*c* includes radioscintigraphic image of three $^{99m}$Tc labeled 100 μm diameter anion exchange beads 375. The radioscintigraphic images of beads were merged with independently acquired images of a tissue surface 377 (mouse leg) to produce the simulated images shown in FIGS. 4*a*-4*c*. FIGS. 4*a*-4*c* illustrate that images indicative of a distribution of radionuclide and of tissue anatomy can provide useful information. As can be seen upon comparing the top view of FIG. 4*a* with the side perspective views of FIGS. 4*b* and 4*c*, system 100 allows an operator to rotate superimposed images to better view distances along different axes of the imaged object. For example, the side views of FIGS. 4*b* and 4*c* clearly reveal the simulated distance between the tissue surface and the beads beneath the surface.

The views in FIGS. 4a-4c were obtained with a coded aperture mask having lower resolution than the 8987 aperture mask described above. Nonetheless, the average FWHM resolution for the three beads is 0.9 mm in x-y plane parallel to the coded aperture mask and 1.7 mm along the z-axis perpendicular to the coded aperture mask. The 8987 aperture mask will exhibit higher resolution in each dimension.

The images of FIGS. 4a-4c, were reconstructed using a Dell desktop running Microsoft® Windows XP® on a 2.5 GHz Pentium® 4 processor with a 533 MHz system bus, 512K cache, 2 GB RAM, and a 120 GB 7200 RPM hard drive with cache. The volume reconstructed was $2^3$ cm using $40^3$ voxels, each 0.5 mm on a side. Starting from an initial object estimate filled uniformly with radioactivity, the reconstruction was completed to maximum resolution in about 19 minutes with 34 iterations, although the beads were clearly visualized after just two iterations.

The number of iterations required depends upon the size and concentration of the radioactive regions and the background activity within the object volume. For small, highly concentrated objects with little background as few as about 5 to about 10 iterations may be sufficient, while for large, diffuse objects with high background as many as 50 to about 100 iterations may be required to achieve an optimal reconstruction.

In some embodiments, processor 106 includes a parent processor and a plurality of child processors. Each child processor is generally configured to calculate the sum in Eq. 1 for a slice having a respective distance along the z-axis. The sums calculated by each processor are combined and used to calculate the updated expected intensity for each detector element Dk. The updated Dk values are returned to each child processor, which compute the new estimate of the radioactivity distribution according to Eq. 2.

Parallel processing reduces reconstruction times because the calculation of Eqs. 1 and 2 are distributed. Also, the burden of storing the probability matrix, Pik, is shared by the child processors, greatly reducing the I/O time required to read Pik values from the disk. For example, a processor including 40 child processors, each having 240 MB of RAM, could easily hold the $(30^2) \times (512^2) = 2.4 \times 10^8$ entries required for a single image slice. Thus, on a parallel processing platform the enormous I/O overhead associated with the probability matrix is virtually eliminated. For example, forty 3 GHz processors could prepare iteratively corrected tomographic images in about 12 seconds or less.

In some embodiments, initial radioscintigraphic images are prepared using an initial resolution to identify regions of increased radioactivity. For example, an object may be represented using a lattice of, e.g., about $10^3$:2 cm voxels. Subsequent images are prepared using higher resolutions, possibly covering smaller fields of view. For example, an object may be represented using a lattice of, e.g., about $40^3$:2 mm voxels. Such higher resolution images can be particularly useful after an initial resection, e.g., when an operator is seeking residual tumor cells.

In some embodiments, the coded aperture data is obtained using a mask that transmits a portion of the radiation, even through the substrate of the mask. The radiation detected in such a configuration can be thought of as resulting from (a) a first portion passing through the substrate of the mask and (b) a second portion passing through the apertures of the mask. The first portion of radiation transmitted through the substrate, as compared to the second portion of radiation transmitted by the apertures, provides less information regarding the distribution of radionuclide within an imaged object. Accordingly, processing the coded aperture data may include preparing image data of the distribution of radionuclide based on the second portion of radiation, e.g., as opposed to or substantially excluding the first portion of radiation.

In some embodiments, the amount or amplitude of the first portion of radiation is determined by detecting radiation from an amount of the radionuclide, e.g., an essentially point source of the radionuclide. The point source may have a maximum dimension of less than about 10 mm, 5 mm, or 2.5, mm or less. Radiation from the amount of radionuclide is detected (a) with a mask intermediate the radionuclide and detector and (b) with the mask not-intermediate the radionuclide and detector. The relative amount of radiation transmitted by the substrate of the mask as opposed to the apertures of the mask can be determined based upon (i) the amount of radiation detected in (a) with the mask intermediate, (ii) the amount of radiation detected in (b) with the mask not-intermediate, and (iii) the relative areas of the apertures and substrate of the mask. Once the relative transmission of the substrate of the mask is known, the first portion of radiation resulting from substrate transmission can be subtracted from other measurements using the same radionuclide (or one of similar energy) and the same mask (or one of similar composition and dimensions).

In some embodiments, the region around the imaged object, e.g., a table supporting a patient, is shielded with lead. The shielding reduces spurious gamma rays reaching the detector 152. In general, the shielding leaves a hole large enough for gamma rays corresponding to the desired field of view to reach the detector.

The final 3D nuclear images will be displayed using IDL running within LabVIEW®, where they will each be overlaid with a current color video image of the surgical anatomy (color video) and/or NIR fluorescence images, and also displayed for the surgeon side-by-side on dual monitors.

Calibration Standards for Multi-Modality Imaging

Figure 5:
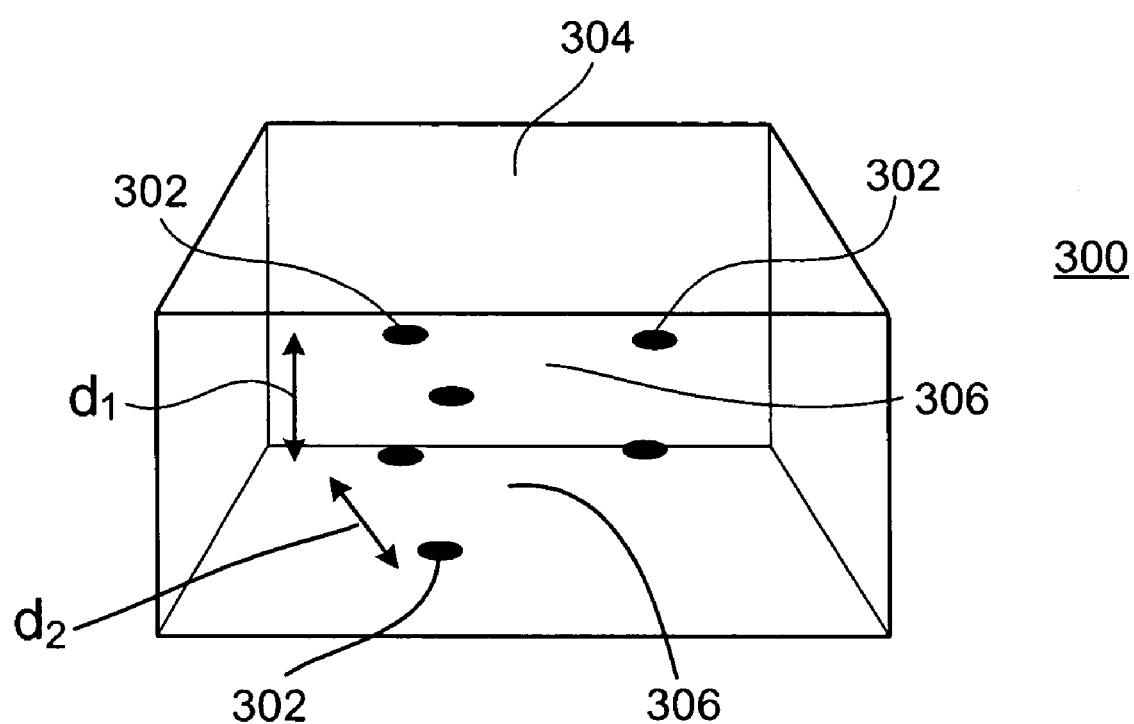
FIG. 5 is schematic diagram of a calibration standard for calibrating optical fluorescence imaging systems and radioscintigraphic imaging systems.

FIG. 5 shows a calibration standard 300 that includes six calibration sites 302, each site 302 being detectable using each of at least two different modalities, e.g., fluorescence, e.g., NIR fluorescence, radioscintigraphy, magnetic resonance imaging, ultrasound, or computer assisted tomography. Calibration sites 302 are supported by a substrate 304, which is transmissive with respect to both the fluorescence and radiation emitted by the sites 302. In some embodiments, the substrate 304 is formed of a polymer, e.g., a plastic such as an acrylic.

Calibration sites 302 are typically configured within at least two different planes 306. Each plane 306 contains at least three calibration sites 302. A distance $d_1$ between the planes 306 is generally about equal or somewhat larger than the worst resolution of the radioscintigraphic system 104 along a dimension perpendicular to the coded aperture mask. In some embodiments distance $d_1$ is about 0.5 cm, 0.75 cm, 1 cm, 1.25 cm, or 1.5 cm, although larger or smaller distances may be used.

Within each plane 306, a distance $d_2$ (the in-plane separation) between nearest calibration sites 302 is generally about equal to the resolution of the radioscintigraphic system 104 in a plane parallel to the coded aperture mask. In some embodiments, the in-plane separation between sites is about 0.1 cm, 0.2 cm, 0.3 cm, or 0.5 cm, although larger or smaller site separations may be used.

Each calibration site 302 generally has a size of less than a minimum separation between nearest sites. For example, the sites may have a maximum dimension, e.g., a diameter, of 2 mm or less, 500 microns or less, 250 microns or less, or about 100 microns or less, although larger or smaller dimension sites may be used. Superparamagnetic iron oxide can be used. Perfluorocarbons can be used.

In some embodiments, each calibration site 302 is a single calibration reference that includes both a fluorescent compound and a radionuclide. An exemplary calibration reference is an ion exchange resin incubated with a fluorescent compound, e.g., and indocyanine green, and a radionuclide-containing compound, e.g., $^{99m}$Tc-pertechnetate. The resin can be an anion exchange resin or a cation exchange resin. An exemplary calibration reference is an anion exchange resin shaped as a bead having a diameter of between about 75 microns to about 2,000 microns.

The calibration standards may include agents detectable by other imaging modalities. Exemplary agents include MRI contrast agents, ultrasound contrast agents, and x-ray detectable contrast agents. For example, the calibration sites may contain a detectable amount of gadolinium, manganese, and/or iron. Gadopentetate dimeglumine, gadoteridol, or gadoterate meglumine may be used. Typically, a high mass (e.g., high z number element) is used in an x-ray and/or ultrasound detectable site.

In some embodiments, each site exhibits an activity of at least about 1 μCi, e.g., at least about 5 μCi. Ion exchange calibration references including fluorescent compounds are described in the paper English et al., "Sub-millimeter technetium-99 m calibration sources," Mol. Imag. Biol., 2002, 4:380-384.

Registration of Optical and Radioscintigraphic Images

Registration of optical and radioscintigraphic images includes determining a spatial relationship between optical data (or images) provided by optical imaging system 102 and radioscintigraphic data (or images) provided by radioscintigraphic imaging system 104. Registered optical and radioscintigraphic modalities can be displayed in a manner that allows a user to visualize the spatial relationship. Typically, the images are displayed as superimposed images.

Registration is typically performed by a method that includes imaging the same object with both optical and radioscintigraphic systems 102, 104. System parameters, e.g., lens focus position and coded aperture mask 150 position, are recorded by processor 106. Subsequently, processor 106 processes the optical and radioscintigraphic data to determine the mathematical manipulation required to co-register or superimpose the images.

Calibration standard 300 can be used to register and/or scale an optical/radioscintigraphic imaging system. In one embodiment, calibration standard 300 is positioned at a location expected to be occupied by an object to be imaged during a procedure. Optical system 102 is focused in the z-dimension upon the nearest plane of calibration sites 302. The optical system z-position and lens position are recorded. Optical system 102 is focused in the z-dimension upon the more distant plane of calibration sites 302 and the focus is adjusted so that the images of the top plane and bottom plane of sites 302 are overlapping. The optical system z-position and focus position are recorded. Radioscintigraphic data is acquired from the two planes of sites 302. The 3-D volume representation of the calibration standard 302 is reconstructed from these data.

Processor 106 can use the optical and radioscintigraphic data of the two planes of calibration sites 302 to register the optical and radioscintigraphic systems with respect to one another in at least one dimension, e.g., the z-axis dimension (FIG. 1). Once the systems have been registered, processor 106 determines the focal location of optical system 102 and processes the radioscintigraphic data of system 104 to provide radioscintigraphic images of the focal location. For example, when an operator of system 100 selects a plane of object 110 to be imaged by focusing lens 115 at a particular focal distance, processor 106 can automatically track the image plane by providing laminographic radioscintigraphic images corresponding to the same plane of the object.

Contrast Agents and Methods of Use

In a typical method of obtaining fluorescence/radioscintigraphic multi-mode images, at least one radionuclide contrast agent (e.g., a nuclear agent) and at least one optical contrast agent (e.g., a fluorescent agent) are mixed together. The mixture is introduced to the subject to provide contrast imaging of a tissue or organ of interest.

The fluorescent compound and/or radionuclide need not be introduced directly to the object. For example, such agents may be introduced to a cancer site while the imaged object includes lymph glands that may be associated with the cancer site. In some embodiments, the fluorescent compound and/or radionuclide is introduced into the bloodstream, e.g., when the fluorescent compound or radionuclide is linked to a targeting ligand.

An exemplary mixture includes at least one of $^{99m}$Tc sulfur colloid having a particle diameter of about 100 nm in an amount sufficient to provide a dose of 100 μCi via intraparenchymal introduction or $^{99m}$Tc-human serum albumin ($^{99m}$Tc-HSA) having a diameter of 7 nm in an amount sufficient to provide a dose of about 100 μCi via intra-parenchymal introduction. The mixture can include NIR quantum dots having a 15 nm diameter in an amount sufficient to provide a dose of about 400 pmol via intra-parenchymal introduction and/or $^{99m}$Tc-HSA in an amount sufficient to provide a dose of about 400 pmol via intra-parenchymal introduction. In some embodiments, a mixture of $^{99m}$Tc-HSA and/or NIR quantum dots and one or more $^{99m}$Tc-labeled lymph tracers is introduced to the subject. $^{99m}$Tc-sestamibi, $^{99m}$Tc-tetrofosmin, and $^{99m}$Tc-MDP (methylene diphosphonate) can also be used.

Contrast agents for sentinel lymph node mapping are typically anionic to improve uptake by lymphatics and retention in the sentinel lymph node. A useful contrast agent has a diameter of at least about 5 nm, 7 nm, 10 nm, e.g., or 15 nm although smaller sizes may be used.

In general, the mixture is introduced directly or indirectly with image guidance into the parenchyma of a tissue, e.g., a tissue of the skin, breast, lung, bladder, or colon. For the skin, a subdermal injection site may be used. For the breast, injection is generally directly into mammary tissue. After co-injection of the contrast agent mixture, lymph channels can be mapped in real-time using system 100.

The time required for obtaining radioscintigraphic images using system 100 can be short. For example, with a coded aperture mask configured with the z-axis vertical and viewing through 15 cm of tissue, about 100 μCi of contrast agent injected (about 5 μCi migrates to the sentinel lymph node), a radioscintigraphic image can be acquired in 31 sec with a signal to background ratio (S/N) of 5. With the coded aperture mask positioned with the z-axis horizontal and viewing through 5 cm of tissue, a radioscintigraphic image can be acquired in 0.7 sec with a S/N of 5. With the coded aperture mask positioned above the surgical site and viewing though about 1 cm of tissue, a radioscintigraphic image having a S/N of 5 can be acquired in 0.2 seconds. These S/N ratios assume a 4×4×4 mm sentinel lymph node, 100% shielding of the injection site, no energy discriminator rejection of scattered photons, and uniform background in the image due to scattered photons.

Assisted by display of optical and radioscintigraphic images, an operator may identify and resect the sentinel lymph node. After resection, the surgical field may be inspected using one or both of the optical and radionuclide imaging systems to ensure that no residual lymph tissue has been left behind. Because detection systems 102 and 104 have a finite dynamic range, some active sites may not be apparent in an initial image with a significant amount of fluorescence and/or radioactivity. Once the most active site is removed, however, a subsequent image may reveal sites of lower, but still problematic, activity. If further active sites are identified, these may be resected. The process can be repeated until no further active sites are observed.

System 100 can allow color video, NIR fluorescence, and radioscintigraphic images, to be acquired, merged, and displayed in a time of less than 60 seconds, less than 45 seconds, less than 30 seconds, less than 20 seconds, less than 10 seconds, less than 5 seconds, or less than 3 seconds. The majority of this time is occupied by acquisition of the radioscintigraphic image, which time is proportional to, and controllable by varying the injected dose. Because the acquisition and display of the optical and radioscintigraphic images are independent, optical images can be obtained and displayed in real-time with 3-D radioscintigraphic images acquired and updated on an intermittent time basis.

Contrast Agent Synthesis

Various contrast agents useful in the new methods and systems can be prepared synthesized or obtained commercially. For example, near-infrared quantum dots can be synthesized as described in the paper Kim, S. et al., "Near-infrared fluorescent type II quantum dots for sentinel lymph node mapping," Nat Biotechnol, 2004, 22(1):93-7.

The contrast agent $^{99m}$Tc-HSA can be synthesized by conjugating the NUS ester of MAS3 with HSA in phosphate buffered saline (PBS), pH 7.8. The NHS ester of MAS3 is described in the paper Chang et al., "NHS-MAS3: A Bifunctional Chelator Alternative To NHS-MAG3," Appl. Radiat. Isot. 1999, 50(4):723-32. After one hour with constant mixing at room temperature, MAS3-HSA can be purified by separation on a Biologics LP (Bio-Rad) chromatography system equipped with a P6 gel filtration column. The substitution ratio can be determined using MALDI-TOF mass spectroscopy, with a desired ratio being 1:1. After purification, glycerol is added to a final concentration of 10%, and the MAS3-HSA flash frozen in liquid $N_2$, and stored at $-80°$ C., until use.

For $^{99m}$Tc loading, 100 µg of MAS3-HSA is typically dissolved in 100 µL ammonium acetate, pH 5.2 supplemented with 20 µL of fresh 50 µg/ml disodium tartate in 0.5 M NaHCO$_3$ and 0.75 M ammonium hydroxide (pH 9.3). About 2 mCi 99 m Tc-pertechnetate (about 20 µL), eluted with saline from a 99 Mo generator is added to the MAS3-HSA followed by 2 µL of a fresh 1 µg/ml solution of $SnCl_2$ in 10 mM HCl. Labeling generally proceeds for 1 hour at room temperature, with the final pH of the reaction being about 7.2. Final gel-filtration of the product can be accomplished on a Waters HPLC system equipped with a 8×300 mm, 5,500 MW cutoff Diol gel filtration column (YMC). Analysis of purity can be accomplished using a 10-1,100 kDa Diol column (YMC). Typical radiochemical yields are about 85-90%.

The contrast agent HSA78 is a covalent conjugate of IRDye78 with human serum albumin. Peak optical absorption is at 771 nm and peak fluorescence emission is at 802 nm. The total quantum yield is equivalent to 2.6 molecules of unconjugated dye. HSA78 is an excellent lymph tracer, demonstrating reproducible chemistry and high in vivo stability. This contrast agent can be synthesized by conjugating the NHS ester of IRDye78 (LI-COR, Lincoln, Nebr.) to human serum albumin in PBS (pH 7.8). Labeled product is purified by P6 gel-filtration chromatography as described above for MAS3-HAS, and the substitution ratio determined by absorbance spectroscopy (Ocean Optics). Substitution can be confirmed using MALDI-TOF mass spectroscopy. A substitution ratio of about 3.4:1 results in the highest fluorescence yield from HSA. HSA78 in PBS, pH 7.4 can be supplemented with 10% (final) glycerol, flash frozen in LN2, and stored at $-80°$ C. until use.

EXAMPLES

The invention is further described in the following examples, which do not limit the scope of the invention described in the claims.

Radioscintigraphic coded-aperture imaging, either alone or in combination with other imaging modalities, can be used in diagnostic and surgical procedures.

Example 1

Sentinel Lymph Node Mapping

Combined optical/radioscintigraphic Sentinel Lymph Node Mapping was done a Yorkshire pig, as an animal model that approaches the size of human patients.

Figure 6A:
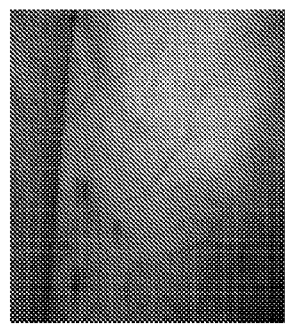
FIGS. 6A to 6F are a series of optical, near IR, nuclear, and combined images taken from a pig used for sentinel lymph node mapping using the systems and methods described herein.
Figure 6B:
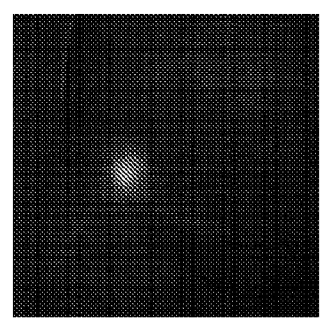
Figure 6C:
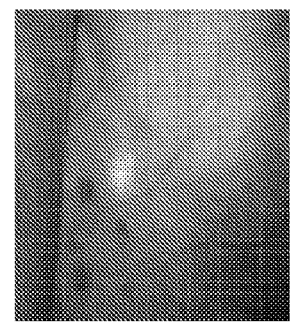

For this experiment, 50 µCi of $^{99m}$Tc sulfur colloid was mixed with 200 pmol of near-infrared fluorescent quantum dots, as described previously (Kim et al., Nat. Biotechnol., 22:93-97, 2004), in a total volume of 100 µL. After injection into the right foot of a 35 kg Yorkshire pig, image guidance was used to follow lymph flow to the groin, identify the SLN in real-time (FIGS. 6A-6F), resect the sentinel and nearby nodes, inspect the resection site, and image the resected nodes. FIG. 6A shows a color video of the pig skin in the vicinity of right foot and groin. FIG. 6B shows the NIR fluorescence image of the same region. FIG. 6C shows the color and NIR images merged.

Figure 6D:
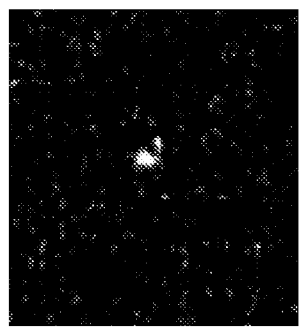
Figure 6E:
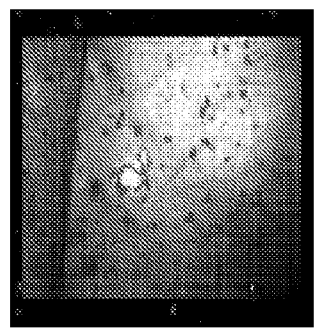
Figure 6F:
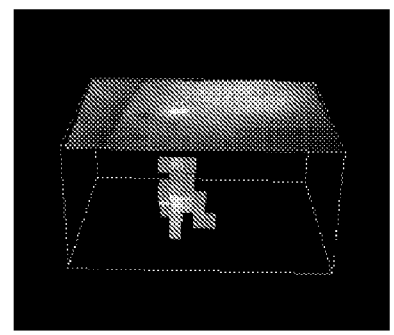

FIG. 6D shows the 2-D laminographic reconstruction of the coded aperture radioscintigraphic image of the same region of the pig. FIG. 6E shows the optical color image, the NIR image, and the nuclear image combined in 2-D, and FIG. 6F shows the 3-D image formed by iterative reconstruction as described herein, with the optical image shown on the surface of the 3-D space.

In another example, a surgeon performs a sentinel lymph node mapping procedure on a human patient by first injecting a fluorescent compound and a radionuclide intra-parenchymally as a mixture into a cancer site of an 80 kg human. The mixture includes an amount of $^{99m}$Tc sulfur colloid having an average particle diameter of 100 nm sufficient to provide a dose of 100 µCi. The mixture also includes an amount of near-infrared fluorescent quantum dots.

The fluorescent and radionuclide compounds travel along the lymph ducts from the cancer site to the sentinel lymph node of the patient. Fluorescent and radioscintigraphic data of tissue surrounding the cancer site are obtained. Reflected light optical data is obtained in the form of color video images. The data are processed to prepare images.

The images are displayed to provide the surgeon with visualization of the anatomy of the surgical field, the location of lymph ducts and the location of the sentinel lymph node. The reflected light image provides the surgeon with information regarding the anatomy of the surgical field generally. The fluorescent image provides information regarding the locations of fine structures near the surface of the tissue surrounding the lymph node. The radioscintigraphic image provides information regarding structures beneath the surface of the tissue. The images are superimposed to provide the surgeon with information indicative of a spatial relationship between the anatomy and the distributions of the fluorescent compound and radionuclide. Assisted by these images, the surgeon resects tissue, e.g., the sentinel lymph node.

In another example, a surgeon performs a sentinel lymph node mapping procedure. A fluorescent compound and a radionuclide are introduced via intra-parenchymal injection as a mixture into a cancer site of an 80 kg human. The mixture includes an amount of $^{99m}$Tc sulfur colloid having a particle diameter of 100 nm sufficient to provide a dose of 100 μCi. An amount of fluorescent compound, indocyanine green, is injected intravascularly.

The radionuclide compound travels from the cancer site to the sentinel lymph node of the patient. Fluorescent and radioscintigraphic data of tissue surrounding the cancer site are obtained. Reflected light optical data is obtained in the form of color video images. The data are processed to prepare images.

The images are displayed to provide the operator with visualization of the anatomy of the surgical field, the location of lymph ducts and the location of the sentinel lymph node. The reflected light image provides the operator with information regarding the anatomy of the surgical field generally. The fluorescent image provides information regarding the locations of venous structures near the surface of the tissue surrounding the lymph node.

Example 2

Scintimammograph

A surgeon performs a scintimammography procedure either as a screening procedure alone or as a screening procedure in combination with a surgical procedure to remove tumor material. The PET pharmaceutical $^{18}$F-FDG is introduced intravenously into a human female subject in an amount sufficient to provide a dose of 10 mCi. A coded aperture radioscintigraphic system detects 511 keV gamma rays resulting from the $^{18}$F to obtain radiation detector data. The data are processed to prepare an image of the distribution of the $^{18}$F within the breast. Based upon the imaged distribution, the surgeon determines whether a tumor or malignancy is present in the tissue.

The surgeon optionally resects an amount of tissue from within the breast. Upon resecting a first portion of tissue, the surgeon again images the breast to detect the distribution of remaining $^{18}$F. Guided by the new images, the surgeon removes additional tissue from the breast and repeats the process until further images do not indicate the presence of tumors or malignant cells.

In another example, a surgeon performs a scintimammography procedure either as a screening procedure or as a screening procedure in combination with a surgical procedure to remove tumor material. $^{99m}$Tc-sestamibi, $^{99m}$Tc-tetrofosmin, or $^{99m}$Tc-MDP (methylene diphosphonate) is introduced intravenously into a human female subject in an amount sufficient to provide a dose of 10 mCi. A coded aperture radioscintigraphic system detects gamma rays resulting from the $^{99m}$Tc compound to obtain radiation detector data. The data are processed to prepare and image of the distribution of the $^{99m}$Tc compound within the breast. Based upon the imaged distribution, the surgeon determines whether a tumor or malignancy is present in the present.

Example 3

Radioscintigraphy with a Mask that Transmits at Least a Portion of the Radiation A coded aperture mask was used to image 511 KeV photons, and an iterative algorithm as described herein was used to reconstruct images of a distribution of a radionuclide emitting the photons in three dimensions. Imaging with the mask mounted on a stationary gamma-camera provided tomographic information about the distribution of PET isotopes from a single data acquisition, despite high transmission through the mask.

A stationary, single-head gamma camera (Isocam II) with a ½" crystal and detector resolution of 2.7 mm was employed. The mask was drilled tungsten alloy K1700® (Kulite Tungsten, Inc.; 92.5% tungsten of density 17.5 g/cm$^3$), 19 cm×19 cm×4 mm thick (56% attenuation at 511 KeV), with 720 holes, each 2.3 mm in diameter, arranged in an anti-symmetric MURA-NTHT pattern. The holes of the mask had a relative area of 0.125 compared to the substrate. The depth of each hole was 4.0 mm. The resolution (at FoV=9 cm) was 2.85 mm. The magnification was 2.6 to 4.0.

Tomographic images of multiple 1 mm F-18-labeled spherical sources were reconstructed by Fourier deconvolution (laminography) and compared to reconstructions obtained using an iterative OSEM algorithm, and to clinical PET/CT. Data was obtained from F-18 radionuclide in a first acquisition with the mask intermediate the detector and in a second acquisition with the mask removed from the detector field of view. Also, two data acquisitions (mask:anti-mask) were used to correct laminographic images for near-field artifacts. OSEM images were reconstructed from a single acquisition.

Both the laminography and OSEM algorithms successfully reconstructed quantitative tomographic images of multiple bead phantoms, over a 10.8 cm cubic FOV, without near-field artifacts. The measured FWHM of the coded aperture system in the x,y dimension was 2.8 mm. The Z-resolution was 7.8 mm by laminography and 4.2 mm by OSEM (all +/−0.3 mm). Beads separated by 6 mm center-to-center were clearly resolved with 1 M total counts.

Positron Emission Tomography (PET) takes advantage of the two nearly back-to-back photons emitted when a positron annihilates an electron. Detection of the two photons defines a line-of-response along which the annihilation must have occurred. Since detection of two photons in coincidence defines a direction, no collimator is needed. The PET scanner is typically constructed as an annulus of detectors. Due to the geometry of the lines-of-response, the data is generally used to produce only tomographic image volumes. PET scanners use scintillation crystals with higher stopping power to improve sensitivity at 511 keV. Furthermore, there is a dramatic increase in sensitivity compared with single photon imaging since no collimator is needed. However, sensitivity is somewhat reduced because both photons from a positron annihilation must be detected. The detector efficiency changes as a squared factor in PET sensitivity. The net of these various affects is that PET imaging is considerably more sensitive than single photon imaging. PET scanners have a large advantage in resolution over single photon imaging of positron emitters. Anger camera resolution is largely determined by collimator resolution, whereas PET resolution is often dominated by the physical size of the crystals.

Transmission by the mask substrate is especially problematic for high energy gamma rays, such as the anti-parallel 511 keV rays emitted during positron annihilation. For example, to minimize mask transmission to essentially zero, the substrate thickness would have to be increased to a point where each hole behaved like a collimator.

Radioscintigraphic data from the F-18 radionuclide was collected using a point source of the radionuclide (i.e., a bead comprising the radionuclide). Data was collected with the mask intermediate the point source and detector and with the mask out of the field of view of the detector. Based on the relative open area of the mask and the collected data, the count rate due solely to transmission through the substrate of the mask (as opposed to through holes of the mask) was determined. The count rate due to substrate transmission adds a noisy constant to the data in each detector pixel. Hence, the count rate due to substrate transmission was subtracted from each pixel of subsequent images prior to Fourier deconvolution. The correction resulted in significant improvement in image contrast of the raw data. Similar correction and improvement is possible for Tc-99m and other isotopes.

Figure 7A:
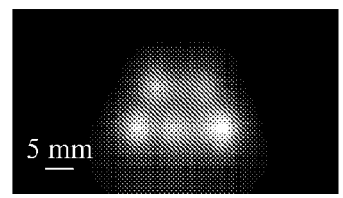
FIGS. 7A and 7B are a pair of images of submillimeter multi-modality point sources (beads) that emit radiation.
Figure 7B:
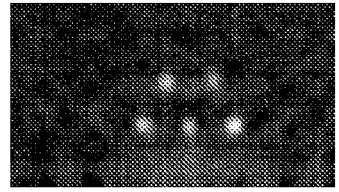

An object consisting often 1 mm beads, each with 5-10 µCi F-18 was imaged using the coded aperture mask and clinical PET/CT scanning. Both laminographic and OSEM processing of the imaging data provided better resolution of the beads than the clinical PET/CT imager. At least a 3 mm improvement in resolution was observed for laminography and a greater improvement for OSEM. FIGS. 7A and 7B show the comparison of the image of the beads as obtained from a clinical PET/CT scanner (FIG. 7A) and from the new coded aperture system (FIG. 7B). Both figures show the beads in a plane parallel to the mask.

Figure 8:
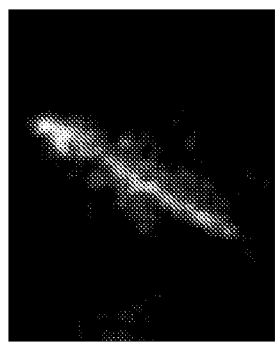
FIG. 8 is a $^{18}$NaF bone scan of a mouse obtained using the new systems and methods described herein.
Figure 8:
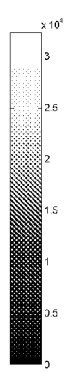

A 25 g mouse was injected (intravenously) with 250 µCi of the bone seeking agent $^{18}$NaF. The coded aperture mask was used to image the skeleton (excluding the tail, which was obstructed by a 4 mm Kulite shield, which also obstructed the injection site and bladder). As shown in FIG. 8, the skull, shoulders, and spine were well visualized in the coded aperture images, although arms are not seen due to limited dynamic range.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

For example, the imaging systems and methods described herein can be used to monitor the introduction of an object, e.g., a catheter, a stent, a robotic surgery device, or a sensor, to a human or animal. The systems and methods can also be used as part of a gene therapy procedure or procedure including the introduction of stem cells into a person or animal. For example, the stem cells can be labeled with or be in contact with a fluorescent compound to permit visualization by an optical imaging system. An imaging system can also include an ultrasound imaging system configured to obtain ultrasound images of a tissue. The ultrasound images can be merged with radioscintigraphic and/or optical images. The ultrasound images can be used to morph the radioscintigraphic images and/or optical images to provide additional topographic information.

What is claimed is:

1. An imaging system comprising:
   a near-field coded aperture detection system comprising a two-dimensional aperture array and configured to detect radiation emitted by a radionuclide present within an object and to provide a nuclear signal from the detected radiation;
   an optical detection system configured to detect optical radiation from the object and to provide an optical signal from the detected optical radiation; and
   a processor configured to:
      prepare first image data from the nuclear signal;
      prepare second image data from the optical signal; and
      prepare registered data indicative of a spatial relationship in three dimensions between the first and second image data.

2. The imaging system of claim 1, further comprising a display and wherein the imaging system is further configured to display an image comprising, superimposed with one another, the first and second image data registered in three dimensions.

3. The imaging system of claim 1, wherein the radiation emitted by the radionuclide and detected by the near-field coded aperture detection system propagates generally along a detection axis; and one dimension is generally aligned with the detection axis.

4. The imaging system of claim 3, wherein the near-field coded aperture detection system detects radiation from one or more radionuclides present at each of a plurality of distances along the detection axis and wherein the first image data are indicative of the distribution of the one or more radionuclides within the object at a selected distance along the detection axis.

5. The imaging system of claim 1, wherein the processor is configured with an iterative algorithm for preparing the first image data.

6. The imaging system of claim 1, wherein the optical signal is indicative of a reflected light image of the object.

7. The imaging system of claim 1, wherein the optical detection system is configured to irradiate the object with light and to detect fluorescence emitted from the object and wherein the second image data are indicative of the fluorescence emitted from the object.

8. The imaging system of claim 7, wherein the optical detection system is configured to detect fluorescence having a wavelength in the near-infrared, infrared, or a combination thereof.

9. The imaging system of claim 1, wherein the coded aperture detection system is configured to detect radiation emitted by an isotope of fluorine, indium, or technetium, or a combination thereof.

10. The imaging system of claim 1, wherein a field of view of the coded aperture detection system and a field of view of the optical detection system simultaneously comprise an identical portion of the object.

11. The imaging system of claim 1, wherein the imaging system is configured to provide a third detector signal by detecting third radiation from the object, the third radiation having an energy different from energy of the radiation emitted by the radionuclide and from energy of the optical radiation.

12. The imaging system of claim 11, wherein the third radiation comprises visible light; and the processor is configured to prepare third image data from the third detector data and display the third image data simultaneously with the first and second image data.

13. An imaging method comprising:
   introducing one or more radionuclides into a portion of a subject;
   providing a first detector signal indicative of radiation emitted by the one or more radionuclides from the portion of the subject and transmitted by apertures of a coded two-dimensional aperture array;

providing optical image data indicative of an optical image of the portion of the subject; and preparing multi-image data indicative of a spatial relationship in three dimensions between a distribution of the radionuclides within the portion of the subject and the optical image thereof.

14. The method of claim 13, further comprising displaying the multi-image data.

15. The method of claim 13, wherein the radiation transmitted by the apertures of the coded aperture array is emitted from one or more radionuclides located at each of a plurality of different distances from the array, and wherein preparing multi-image data comprises preparing multi-image data indicative of a spatial relationship between a distribution of the one or more radionuclides at a selected distance from the array within the portion of the subject and the optical image thereof.

16. The method of claim 15, wherein the selected distance from the array corresponds to a focus of the optical image of the portion of the subject.

17. The method of claim 15, wherein the multi-image data has a resolution of less than 2.5 cm with respect the selected distance from the array.

18. The method of claim 15, wherein preparing the multi-image data comprises performing an iterative algorithm.

19. The method of claim 13, wherein providing the first detector signal and providing the optical image data are performed without moving the subject intermediate these steps.

20. The method of claim 13, further comprising introducing a fluorescent compound into the portion of the subject, and wherein providing optical image data comprises irradiating the portion of the subject with light; and detecting fluorescence emitted by the fluorescent compound, wherein the optical image data is indicative of the distribution of the fluorescent compound within the portion of the subject.

21. The method of claim 20, further comprising simultaneously displaying the multi-image data and a reflected light image.

22. The method of claim 13, wherein the portion of the subject is breast tissue.

* * * * *

UNITED STATES PATENT AND TRADEMARK OFFICE
CERTIFICATE OF CORRECTION

| | | |
|---|---|---|
| PATENT NO. | : 7,394,053 B2 | Page 1 of 1 |
| APPLICATION NO. | : 11/222864 | |
| DATED | : July 1, 2008 | |
| INVENTOR(S) | : John V. Frangioni et al. | |

It is certified that error appears in the above-identified patent and that said Letters Patent is hereby corrected as shown below:

Title Page, item 56 Other Publications, Accorsi et al. publication: delete the word "Medicint" and replace it with --Medicine--.

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,394,053 B2 | Page 1 of 1 |
| APPLICATION NO. | : 11/222864 | |
| DATED | : July 1, 2008 | |
| INVENTOR(S) | : John V. Frangioni et al. | |

It is certified that error appears in the above-identified patent and that said Letters Patent is hereby corrected as shown below:

Title Page, (73) Assignee: delete "Beth Israel Deaconess Medical Center, Inc., Boston, MA (US)" and replace it with -- Beth Israel Deaconess Medical Center, Inc., Boston, MA (US), Children's Hospital of Philadelphia, Philadelphia, PA (US), and Massachusetts Institute of Technology, Cambridge, MA (US) --

Signed and Sealed this
Twenty-first Day of June, 2011

David J. Kappos
*Director of the United States Patent and Trademark Office*